(12) United States Patent
Babich et al.

(10) Patent No.: US 7,381,399 B2
(45) Date of Patent: Jun. 3, 2008

(54) TECHNETIUM-DIPYRIDINE COMPLEXES, AND METHODS OF USE THEREOF

(75) Inventors: John W. Babich, North Scituate, MA (US); Kevin P. Maresca, Tewksbury, MA (US)

(73) Assignee: Molecular Insight Pharmaceuticals, Inc., Cambridge, MA (US)

( * ) Notice: Subject to any disclaimer, the term of this patent is extended or adjusted under 35 U.S.C. 154(b) by 634 days.

(21) Appl. No.: 10/386,403

(22) Filed: Mar. 11, 2003

(65) Prior Publication Data
US 2003/0235843 A1 Dec. 25, 2003

Related U.S. Application Data

(60) Provisional application No. 60/363,142, filed on Mar. 11, 2002.

(51) Int. Cl.
*A61K 51/00* (2006.01)
*A61M 36/14* (2006.01)

(52) U.S. Cl. .................. 424/9.1; 424/1.11; 424/1.69; 424/1.65

(58) Field of Classification Search ............... 424/1.11, 424/1.65, 1.69, 9.1, 9.3, 9.4, 9.5, 9.6, 9.7, 424/9.8, 1.49, 1.73, 1.37; 534/7, 10–16
See application file for complete search history.

(56) References Cited

U.S. PATENT DOCUMENTS

2002/0061599 A1 5/2002 Elling et al. ................. 436/518

OTHER PUBLICATIONS

Okuno et al (Polyhedron, 1997, vol. 16, No. 21, pp. 3765-3774).*
Banerjee, S. R. et al. "{Re$^{111}$Cl$_3$} Core Complexes with Bifunctional Single Amino Acid Chelates" *Inorganic Chemistry* 2002, 41, 5795-5802.
International Search Report, PCT Application No. PCT/US03/07328, mailed Jun. 17, 2004.
Alberto et al.; "A Novel Organometallic Aqua Complex of Technetium for the Labeling of Biomolecules: Synthesis of [ $^{99m}$Tc ( OH$_2$ )$_3$ (CO )$_3$]$^+$ from $^{99m}$Tc O4] In Aqueous Solution and Its Reaction with a Bifunctional Ligand", J. Am. Chem. Soc. 120: 7987-7988, (1998).
Alberto et al.; "Application of Techtium and Rhenium Carbonyl Chemistry to Nuclear Medicine. Preparation of [Net 4] 2 [TcC13 (CO)3] From [NBU4][TcO4] and Structure of [NEt 4][Tc 2(□-Cl) 3 (CO) 6]; Structures of the Model Complexes [NEt 4][Re 2 (□-OA c) (CO) 6] and [Re Br ( {-CH2 S(CH2)2 C1} 2) (CO)3]", Transition Met. Chem., 22: 597-601, (1997).
Davidson et al.; "A New class of Oxotechnetium (5+) Chelate Complexes containing a TcON$_2$S$_2$ Core", Iorganic Chemistry 20(6): 1629-1632, (Jun. 1981).
Kung et al.; "New Tc-99 Complexes Based on N2 S2 Ligands", The Journal of Nuclear Medicine, 28(6): 1051 (Abstract No. 719), (Jun. 1986).
Hom and Katzenellenbogen. "Technetium-99m-Labeled Receptor-Specific Small Molecule Radiopharmaceuticals: Recent Developments and Encouraging Results", Nuclear Medicine & Biology 24: 485-498, (1997).
Kung et al.; "Synthesis and Biodistribution of Neutral Lipid-soluble Tc-$^{99m}$ Complexes that Cross the Blood-Brain Barrier", The Journal of Nuclear Medicine, 25: 326-332, (1984).
Kung et al.; "Synthesis of New Bis(aminoethanethiol) (BAT) Derivatives: Possible Ligands for $^{99m}$Tc Brain Imaging Agents", J. Med. Chem. 28: 1280-1284, (1985).
Maresca et al.; "Synthesis and Characterization of a Binuclear Rhenium Nitropyrazole Complex [Re$_2$ O$_3$ Cl$_2$ (PPh$_3$)$_2$ (C$_3$ H$_2$ N$_3$O$_2$)$_2$ ]", Inorganica Chimica Acta, 260: 83-88, (1997).
Maresca et al.; "Cationic Complexes of the '3+1' Oxorhenium□thiolate Family", Inorganica Chimica Acta, 297: 98-105, (2000).
Nicholson et al.; "The Synthesis and Characterization of [MCl$_3$ (N=NC$_5$H$_4$NH) (HN=NC$_5$H$_4$N) ] from [MO$_4$] □ (Where M= Re, Tc) Organodiazenido, Organodiazene-Chelate Complexes. The X-Ray Structure of [ ReCl$_3$ (N=NC$_5$H$_4$NH) (HN=NC$_5$H$_4$N)]", Inorganica Chimica Acta, 252: 421-426, (1996).
Reedijk, J.; "Medicinal Applications of Heavy-Metal Compounds", Current Opinion in Chemical Biology 3: 236-240, (1999).
Rose et al.; "Synthesis and Charaterization of Organohydrazino Complexes of Technetium, Rhenium, and Molybdnum with the {M( η1-HxNNR) (η2-Hy NNR)} Core and their Relationship to Radiolabeled Organohydrazine-Derivatived Chemotactic Peptides with Diagnostic", Inorg. Chem. 37: 2701-2716, (1998).
Salmain et al.; "Labeling of Proteins by Organometallic Complexes of Rhenium (I). Synthesis and Biological Activity of the Conjugates", Bioconjugate Chen. 4: 425-433, (1993).
Van Staveren et al.; "Spectroscopic Properties, Electrochemistry, and Reactivity of Mo0, MoI, and Mo II Complexes with the [Mo (bpa) (CO)3] Unit [bpa+bis (2-picolyl)amine] and their Application for the Labelling of Peptides", Europ. J. Inorg. Chem., pp. 1518-1529, (2002).

(Continued)

Primary Examiner—Dameron L. Jones
(74) Attorney, Agent, or Firm—Foley & Lardner LLP; Michel Morency; James F. Ewing

(57) ABSTRACT

One aspect of the invention relates to novel complexes of technetium (Tc) with various heteroaromatic ligands, e.g., pyridyl and imidazolyl ligands, and their use in radiopharmaceuticals for a variety of clinical diagnostic and therapeutic applications. Another aspect of the invention relates to novel pyridyl ligands that form a portion of the aforementioned complexes. Methods for the preparation of the technetium complexes are also described. Another aspect of the invention relates to novel pyridyl ligands based on derivatized lysine, alanine and bis-amino acids for conjugation to small peptides by solid phase synthetic methods. Additionally, the invention relates to methods for imaging regions of a mammal using the complexes of the invention.

24 Claims, 3 Drawing Sheets

OTHER PUBLICATIONS

Supplementary Partial European Search Report (EP 03 71 1512); Date of Completion: May 15, 2006; 4 Pages.

Nelson, Samuel Martin et al.; "A Strong-field Non-conjugated Polyamine Ligand: Low-spin Iron (II) and High-spin Nickel(II) Complexes;" Journal of the Chemical Society; 1968; pp. 272-276, even pages only.

Cox, D. D. et al: "Catecholate LMCT Bands as Probes for the Active Sites of Nonheme Iron Oxygenases;" Journal of the American Chemical Society; 1998; pp. 2026-2032, even pages only.

Abufarag, Ahmed et al.; "Zinc Complexes of the Ligand Dipicolylglycine;" Inorganic Chemistry; 1995; pp. 2207-2216, odd pages only.

Schibili, Roger et al.; "Influence of the Denticity of Ligand Systems on the in Vitro and in Vivo Behavior of $^{99m}$Tc(I)-Tricarbonyl Complexes: A Hint for the Future Functionalization of Biomolecules;" Bioconjugate Chemistry; 2000; pp. 345-351, odd pages only.

La Bella, Roberto et al.; "In vitro and in vivo evaluation of a $^{99m}$Tc(I)-labeled bombesin analogue for imaging of gastrin releasing peptide receptor-positive tumors;" Nuclear Medicine and Biology; 2002; pp. 553-560, odd pages only.

Banerjee, Sageeta Ray et al.; Bifunctional Single Amino Acid Chelates for Labeling of Biomolecules with the $\{TC(CO)_3\}+$ and $\{Re(CO)_3\}+$ Cores. Crystal and Molecular Structures of $[ReBr(CO)_3(H_2NCH_2C_5H_4N]$, $[Re(CO)_3\{(C_5H_4NCH_2)_2NH\}]Br$, $[Re(CO)_3\{(C_5H_4NCH_2)_2NCH_2CO_2H\}]Br$, $[Re(CO)_3\{X(Y)NCH_2CO_2CH_2CH_3\}]BR$ (X=Y=2-pyridylmethyl; X=2-pyridylmethyl, Y=2-(1-methylimidazolyl)methyl; X=Y=2-(1-methylimidazolyl)methyl), $[ReBr(CO)_3\{(C_5H_4NCH_2)NH(CH_2C_4H_3S)\}]$, and $[Re(CO)_3\{(C_5H_4NCH_2)N(CH_2C_4H_3S)(CH_2CO_2)\}]$; Inorganic Chemistry; 2002; pp. 6417-6425, odd pages only.

* cited by examiner

TECHNETIUM-DIPYRIDINE COMPLEXES, AND METHODS OF USE THEREOF

RELATED APPLICATIONS

This application claims the benefit of priority to U.S. Provisional Patent Application Ser. No. 60/363,142, filed Mar. 11, 2002.

BACKGROUND OF THE INVENTION

Radiopharmaceuticals may be used as diagnostic or therapeutic agents by virtue of the physical properties of their constituent radionuclides. Thus, their utility is not based on any pharmacologic action per se. Most clinically used drugs of this class are diagnostic agents incorporating a gamma-emitting nuclide which, because of physical, metabolic or biochemical properties of its coordinated ligands, localizes in a specific organ after intravenous injection. The resultant images can reflect organ structure or function. These images are obtained by means of a gamma camera that detects the distribution of ionizing radiation emitted by the radioactive molecules.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

Many of the procedures presently conducted in the field of nuclear medicine involve radiopharmaceuticals which provide diagnostic images of blood flow (perfusion) in the major organs and in tumors. The regional uptake of these radiopharmaceuticals within the organ of interest is proportional to flow; high flow regions will display the highest concentration of radiopharmaceutical, while regions of little or no flow have relatively low concentrations. Diagnostic images showing these regional differences are useful in identifying areas of poor perfusion, but do not provide metabolic information of the state of the tissue within the region of apparently low perfusion.

It is well known that tumors often have regions within their mass which are hypoxic. These result when the rapid growth of the tumor is not matched by the extension of tumor vasculature. A radiopharmaceutical which localizes preferentially within regions of hypoxia could be used to provide images which are useful in the diagnosis and management of therapy of tumors, as suggested by Champman, "Measurement of Tumor Hypoxia by Invasive and Non-Invasive Procedures—A Review of Recent Clinical Studies", Radiother. Oncol., 20(S1), 13-19 (1991). Additionally, a compound which localizes within the hypoxic region of tumors, but is labeled with a radionuclide with suitable alpha- or beta-emissions could be used for the internal radiotherapy of tumors. In the brain or heart, hypoxia typically follows ischemic episodes produced by, for example, arterial occlusions or by a combination of increased demand and insufficient flow.

However, many radionuclides are less than ideal for routine clinical use. For example, the positron-emitting isotopes (such as $^{18}F$) are cyclotron-produced and short-lived, thus requiring that isotope production, radiochemical synthesis, and diagnostic imaging be performed at a single site or region. The costs of procedures based on positron-emitting isotopes are very high, and there are very few of these centers worldwide. While $^{123}I$-radiopharmaceuticals may be used with widely-available gamma camera imaging systems, $^{123}I$ has a 13 hour half-life (which restricts the distribution of radiopharmaceuticals based on this isotope) and is expensive to produce. Nitroimidazoles labeled with $^{3}H$ are not suitable for in vivo clinical imaging and can be used for basic research studies only.

A number of factors must be considered for optimal radioimaging in humans. To maximize the efficiency of detection, a radionuclide that emits gamma energy in the 100 to 200 keV range is preferred. To minimize the absorbed radiation dose to the patient, the physical half-life of the radionuclide should be as short as the imaging procedure will allow. To allow for examinations to be performed on any day and at any time of the day, it is advantageous to have a source of the radionuclide always available at the clinical site.

A variety of radionuclides are known to be useful for radioimaging, including Ga-67, Tc-99m, In-111, I-123, and I-131. The preferred radioisotope for medical imaging is Tc-99m. Its 140 keV gamma-photon is ideal for use with widely-available gamma cameras. It has a short (6 hour) half life, which is desirable when considering patient dosimetry. Tc-99m is readily available at relatively low cost through commercially-produced $^{99}Mo/Tc$-99m generator systems. As a result, over 80% of all radionuclide imaging studies conducted worldwide utilize Tc-99m. See generally Reedijk J. "Medicinal Applications of heavy-metal compounds" Curr. Opin. Chem. Biol. (1999) 3(2): 236-240; and Hom, R. K., Katzenellenbogen, J. A. "Technetium-99m-labeled receptor-specific small-molecule radiopharmaceuticals: recent developments and encouraging results" Nuc. Med. and Biol. (1997) 24: 485-498. These advantages, coupled with the fact that Single Photon Emission Computed Tomography cameras are optimized for the 140 keV energy of Tc-99m, clearly demonstrate the superiority of Tc-99m-labeled imaging agents.

Recently, a new Tc(I) labeling system has been developed. Aberto, R., Schibli, R., Egli, A., Schubiger, A. P., Abram, U., Kaden, T. A. "A Novel Organometallic Aqua Complex of Technetium for the Labeling of Biomolecules: Synthesis of $[^{99m}Tc(OH_2)_3(CO)_3]^+$ from $[^{99m}TcO_4]^-$ in Aqueous Solution and Its Reaction with a Bifunctional Ligand" J. Am. Chem. Soc. (1998) 120: 7987-7988; and Alberto, R., Schibli, R., Daniela, A., Schubiger, A. P., Abram, U., Abram, S., Kaden, T. A. "Application of technetium and rhenium carbonyl chemistry to nuclear medicine—Preparation of $[Net_4]_2$ $[TcCl_3(CO)_3]$ from $[NBu_4][TcO_4]$ and structure of $[NEt_4]$ $[Tc_2(u-Cl)_3(CO)_6]$; structures of the model complexes $[NEt_4][Re_2(u-OEt)_2(u-OAc)(CO)_6]$ and $[ReBr(\{-CH_2S(CH_2)_2Cl\}_2(CO)_3]$" Transition Met. Chem. (1997) 22: 597-601. This system takes advantage of the organometallic Tc(I) carbonyl chemistry. Importantly, the chemistry of $[^{99m}Tc(OH_2)_3(CO)_3]^+$ has been elucidated and simplified to the point where the methods are routine and offer a practical alternative to the currently employed Tc(V) chemistry. In contrast to the highly reactive Tc(V)-oxo cores, where the chemistry is sometimes unpredictable and includes labeling cleanup steps, the Tc(I) method offers an attractive labeling alternative. However, unlike the Tc(V)-oxo core, the Tc(I) $(CO)_3^+$ core limits the number of possible coordination geometries available for Tc due to the presence of the three carbonyl groups. The facial arrangement of carbonyl ligands around the metal center also impose steric constraints on the binding possibilities of the remaining three sites.

Moreover, the $[^{99m}Tc(OH_2)_3(CO)_3]^+$ complex can be readily prepared in saline under 1 atm of carbon monoxide (CO). This water and air stable Tc(I) complex is a practical precursor to highly inert Tc(I) complexes, due in part to the $d^6$ electron configuration of the metal center. As already pointed out, the preparation of the organometallic tris(aquo) ion is simple and straightforward, allowing for convenient manipulation and product formation. Substitution of the labile $H_2O$ ligands has been shown to leave the $Tc(CO)_3^+$ core intact. This stable core has the additional advantage of being smaller and less polar than the routinely employed Tc(V)-oxo systems. This characteristic could be advantageous in biologically relevant systems where the addition of the metal center effects the size, shape, and potentially the bioactivity of the compounds.

Although various chelators are currently employed in the binding of tectnetium, all of these tracers suffer from one or more disadvantages which render them less than ideal: HYNIC requires coligands; MAG3 may be only used with the Tc(V)-oxo species; EDTA/DTPA is used primarily with Tc(V)-oxo and its ability to retain label is poor. Hence, additional Technetium-99m chelators are needed. Novel radiolabeled chelators that display rapid, efficient labeling and demonstrate superior labeling retention for both Tc(V)-oxo and Tc(I)-tricarbonyl cores without the use of coligands are attractive candidates for clinical evaluation as potential chelators for biologically relevant molecules.

SUMMARY OF THE INVENTION

Generally, this invention relates to novel complexes of technetium (Tc) with various heteroaromatic ligands, e.g., pyridyl and imidazolyl ligands, and their use in radiopharmaceuticals for a variety of clinical diagnostic and therapeutic applications. Another aspect of the invention relates to novel pyridyl ligands that form a portion of the aforementioned complexes. Methods for the preparation of the technetium complexes are also described. Another aspect of the invention relates to novel pyridyl ligands based on derivatized lysine, alanine and bis-amino acids for conjugation to small peptides by solid phase synthetic methods. Additionally, the invention relates to methods for imaging regions of a mammal using the complexes of the invention.

DETAILED DESCRIPTION OF THE INVENTION

Figure 1:
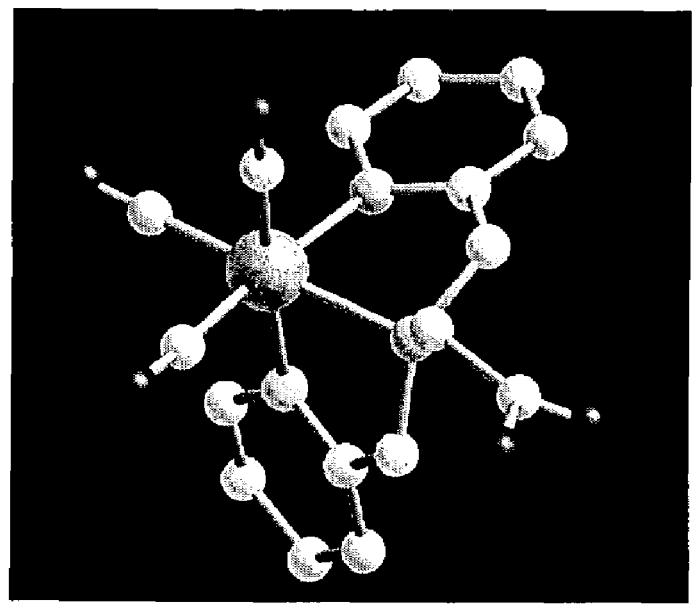
FIG. 1 depicts the structure of [Tc(CO)$_3$(L3a)].

We have developed a novel class of technetium chelating agents based on the derivatization of di(pyridinemethyl) amine (DMPA), a compound that has demonstrated affinity for binding technetium. Specifically described here are the synthesis, radiolabeling, rhenium modeling, and testing of novel radioactive dimethylpyridine derivatives as bifunctional chelators which demonstrate a high binding affinity for Tc-99m, and have been derivatized to become biochemical probes for the assessment of a variety of biological processes, ranging from infection to cancer diagnosis. We have optimized the structural features of a technetium-99m labeled chelate, such that an agent is developed which exhibits high labeling yield, superior retention and the versatility to label both Tc(V)-oxo and Tc(I)-tricarbonyl cores. The dipyridinemethylamine complexes of the present invention allow labeling without the need for the involvement of co-ligands. Eliminating the requirement for a co-ligand dramatically simplifies the labeling procedures of the present invention.

One aspect of the present invention involves the use of di(pyridinemethyl)amine (DPMA) as a tridentate ligand for radionuclides. The ligand demonstrates remarkable ability to rapidly bind both Tc(V)-oxo and Tc(I)-tricarbonyl cores. Notably, the neutral ligand utilizes all three nitrogens as donors to chelate the metal center.

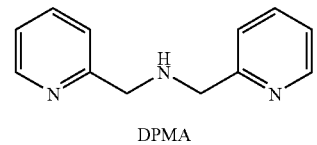

DPMA

Moreover, a biologically relevant molecule, e.g., a peptide or DAT ligand, can be covalently linked to the central nitrogen of the DPMA ligand without interfering with the ligand's ability to chelate the radionuclide. The following drawing depicts this embodiment, wherein R represents a biologically relevant molecule.

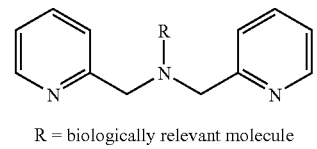

R = biologically relevant molecule

Chelators based on DPMA serve as neutral, i.e., uncharged, tridentate (N—N—N) donors for both the Tc(V)-oxo and Tc(I)-tricarbonyl cores. However, ligands have also been prepared that are cationic or anionic, e.g., depending on the charge of the group (R) attached to the central nitrogen in the structure above. Additionally, the various classes of ligands shown below may be used with the Tc(I)-tricarbonyl core.

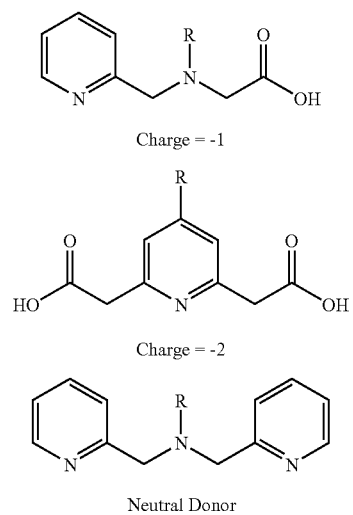

Charge = -1

Charge = -2

Neutral Donor

-continued

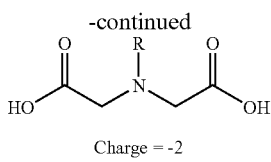

Charge = −2

Another aspect of the present invention relates to development of novel Tc-99m labeled DPMA analogs, and evaluation of their potential as myocardial blood flow imaging agents. The Tc-99m(DPMA) (1) and the Tc-99m(DPMA ethyl ester) (6) complexes were investigated as potential heart imaging agents in rats. The rationale behind these studies is that the chelate is small, lipophilic, and potentially cationic at physiological pH, all of which are characteristics of effective blood flow agents.

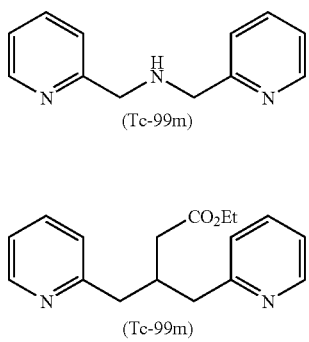

We synthesized a series of novel pendant modified derivatives. A major concern when designing a chelated-Tc-99m labeled pharmaceutical is that the inclusion of the Tc-ligand in the carrier molecule should not drastically alter the biological behavior of the carrier. Therefore, we examined several pendant conjugation techniques. Hom, R. K., Katzenellenbogen, J. A. "Technetium-99m-labeled receptor-specific small-molecule radiopharmaceuticals: recent developments and encouraging results" Nuc. Med. and Biol. (1997) 24: 485-498. In these labeling approaches, the chelated radionuclide is bound to the bio-molecule via a pendant chain distant to the receptor-binding site. Advantages of this design include the ability to change the length and location of the pendant chain, as well as the ability to vary chelating moieties. By adopting these ideas we were able to quickly synthesize a series of versatile chelators that could be functionalized with various biological molecules. Scheme 1 depicts the synthesis of various DPMA derivatives. See Exemplification.

Scheme 1.
Synthesis of various DPMA derivatives.

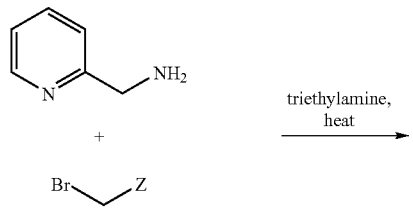

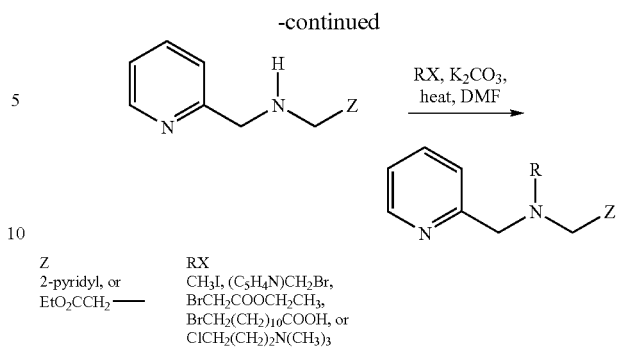

| Z | RX |
|---|---|
| 2-pyridyl, or EtO$_2$CCH$_2$— | CH$_3$I, (C$_5$H$_4$N)CH$_2$Br, BrCH$_2$COOCH$_2$CH$_3$, BrCH$_2$(CH$_2$)$_{10}$COOH, or ClCH$_2$(CH$_2$)$_2$N(CH$_3$)$_3$ |

This work lead to the design of bifunctional chelators constructed from amino acids, so as to provide a donor set for effective coordination of Tc(I) and a linker group for attachment to peptide units. The significance of this ligand design is that the bifunctional chelators may be developed as reagents for direct incorporation into conventional solid phase peptide syntheses (SPPS), thus exploiting the considerable advantages in purity, cost, scale and design afforded by SPPS.

Figure 2:
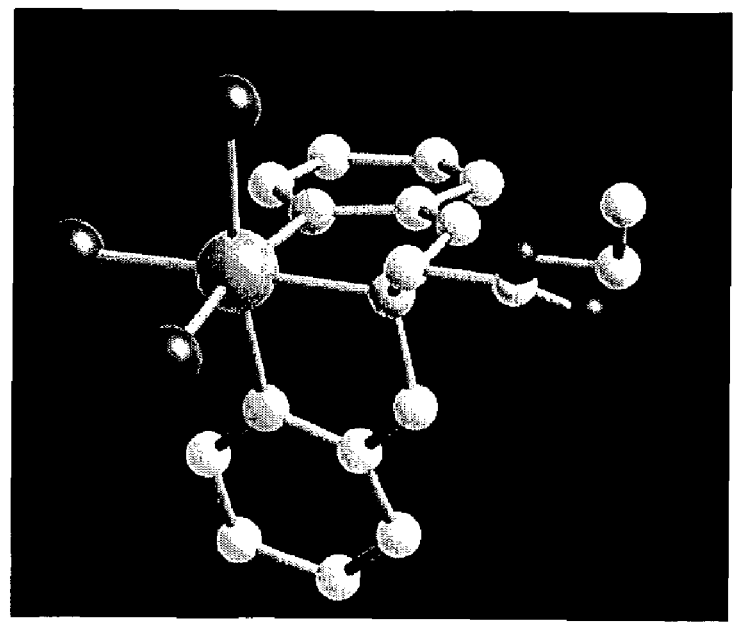
FIG. 2 depicts the structure of [ReCl$_3$(L3a-ethylester)].

In a preliminary study, the alanine derivative (NC$_5$H$_4$CH$_2$)$_2$NCH$_2$CH$_2$CO$_2$H (bis-2-pyridylmethylamino-ethylcarboxylic acid, L3a) was prepared by the methods described below. The Tc(I) complex of L3a [Tc(CO)$_3$(L3a)] (2) was prepared in nearly quantitative yield (FIG. 1), as well as an unusual material exhibiting the rhenium(IV)-trichloride core [ReCl$_3$(L3a-ethylester)](3) (FIG. 2). The facile preparations of these model compounds suggested that a family of bifunctional chelators, derived from simple amino acids or bis-amino acids could be developed, which through suitable manipulation of the ligand donor groups can provide neutral, cationic or anionic Tc(I) complexes.

One goal of the present invention is to develop a family of bifunctional chelators based on pyridyl and/or carboxylate derivatized amino acids or bis-amino acids for conjugation to small peptides by solid phase synthetic methods. To achieve this, lysine, alanine, aminoalanine and a series of bis amino acids will be modified to incorporate a tridentate chelation terminus (A), as well as a terminus (B) for conjugation to small peptides exploiting solid phase synthesis. The optimal design of the tether (C) will also be investigated (Scheme 2).

In certain embodiments, the present invention relates to amino acids, e.g., alpha-amino acids, bearing covalently linked bifunctional chelators for radionuclides, e.g., technetium. For example, the present invention relates to compounds represented by A, wherein R' represents a covalent tether, e.g., a butylene linker as in Lys, between the alpha carbon of the alpha-amino acid and R"; and R" represents a bifunctional chelator for a radionuclide. Exemplary structures for the bifunctional chelator for a radionuclide represented by R" are also depicted below. Amino acids, such as A, bearing a bifunctional chelator for a radionuclide may be used in place of natural amino acids in any of the methods of oligopeptide, polypeptide or protein synthesis, including the methods of automated protein synthesis.

Exemplary embodiments of R″

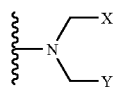

X = Y = 2-pyridyl
X = 2-pyridyl; Y = CO$_2$H
X = Y = CO$_2$H
X = Y = 4-imidazolyl
X = 4-imidazolyl; Y = CO$_2$H Design and Synthesis of the Bifunctional Chelates The "organometallic approach" for functionalization and radiolabeling of target specific biomolecules, pioneered by Jaouen, has received considerable attention in recent years. Salmain, M.; Gunn, M.; Gorfe, A.; Top, S.; Jaouen, G. *Bioconjugate Chem.* 1993, 4, 425. In particular, Tc(I)- and Re(I)-tricarbonyl complexes are ideal candidates for the labeling of receptor avid biomolecules in terms of reduced size and kinetic inertness of their complexes. The $\{M(CO)_3\}^{+1}$ core exhibits particular affinity for nitrogen and oxygen donor ligands and forms robust complexes with such tridentate N,O donor ligands of the general type $[M(CO)_3(N_xO_{3-x})]$, where $N_xO_{3-x}$ is the tridentate chelator. This observation provides the conceptual starting point for the design of our bifunctional chelates for peptide labeling.

As illustrated below in Scheme 3, certain novel bifunctional chelates are derived from lysine, alanine, aminoalanine or bis-amino acids. Since both the identity of the donor groups and the amino acid backbone can be readily modified, the chelator and the linker termini may be optimized for $^{99m}$Tc coordination and peptide conjugation, respectively. Furthermore, by modifying the identities of the chelating donor groups, neutral, anionic and cationic complexes of general types $[M(CO)_3(L1a)]$, $[M(CO)_3(L1b)]^-$ and $[M(CO)_3(L1c)]^+$ may be prepared for different applications. Respresentative ligand syntheses are detailed below for L1c-Boc and L2d-Boc, illustrating the direct and facile methodology.

Scheme 3.
The amino acid-based bifunctional chelates of this study.

ε-derivative lysine, L1

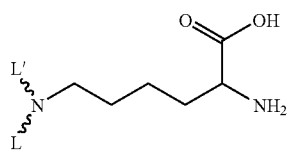

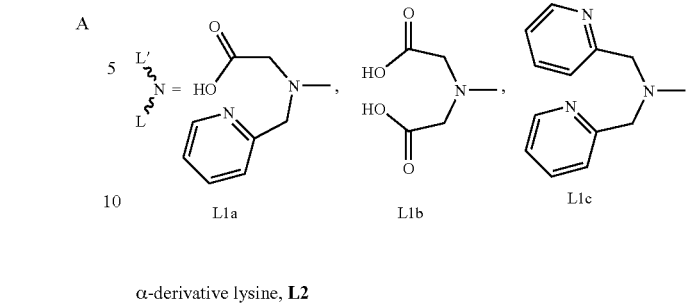

L1a   L1b   L1c

α-derivative lysine, L2

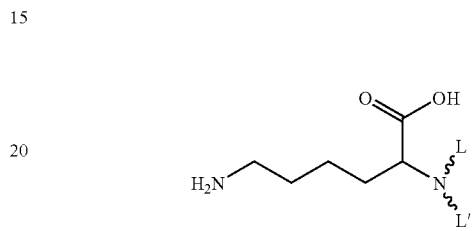

L = ——CH$_2$CO$_2$H, L′ = ——CH$_2$CO$_2$H, L2a
L = ——CH$_2$CO$_2$H, L′ = ——CH$_2$C$_5$H$_4$N, L2b
L = ——CH$_2$CO$_2$H, L′ = ——H, L2c
L = ——CH$_2$C$_5$H$_4$N, L′ = ——H, L2d

BFC analogs based on alanine, L3

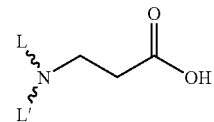

L = ——CH$_2$C$_5$H$_4$N, L′ = ——CH$_2$C$_5$H$_4$N, L3a
L = ——CH$_2$C$_5$H$_4$N, L′ = ——CH$_2$CO$_2$H, L3b
L = L′ = ——CH$_2$CO$_2$H, L3c
L = ——CH$_2$C$_5$H$_4$N, L′ = ——CH$_2$CH$_2$CO$_2$H, L3d

BFC analogs baseds on aminoalanine, L4

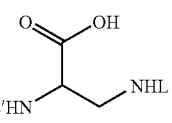

L = ——CH$_2$CO$_2$H, L′ = ——(CH$_2$)$_n$CH$_3$, L4a
L = ——CH$_2$C$_5$H$_4$N, L′ = ——(CH$_2$)$_n$CH$_3$, L4b
L = ——(CH$_2$)$_n$CH$_3$, L′ = ——CH$_2$C$_5$H$_4$N, L4c

BCF analogs of bis amino acids, L5

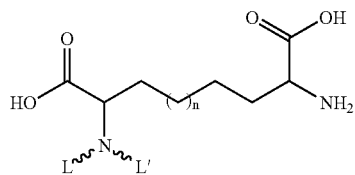

L = ——CH$_2$C$_5$H$_4$N, L′ = ——CH$_2$CO$_2$H, L5a
L = L′ = ——CH$_2$C$_5$H$_4$N, L5b
L = ——CH$_2$C$_5$H$_4$N, L′ = ——H, L5c

At this stage, conventional solid phase synthesis can be exploited to prepare the peptide conjugate. Bodansky, M., *Principles of Peptide Synthesis,* Springer-Verlag: Berlin, 1984; and Bodansky, M.; Bodansky, A., *The Practice of Peptide Synthesis,* Springer-Verlag: Berlin, 1984. The peptide chain can be constructed using FMOC protocols and capped with a BOC protecting group. The bifunctional chelator (BFC) may now be introduced to provide a pendant peptide-BFC design. Alternatively, the bis-amino acid based BFCs may be incorporated into the peptide sequence to provide a variant of the integrated design concept (Scheme 4).

useful technetium-99m, which routinely uses tin-reduced $^{99m}$Tc. Synthesizing the rhenium-dipyridinemethylamine complexes provided a facile route to structurally characterize the products. The characterized products may, in turn, lead to the development of new Tc-DPMA derivatives based on the presence or absence of a structural feature observed in the rhenium data. The periodic relationship between Tc and Re indicates that Tc-99m radiopharmaceuticals can be designed by modeling analogous rhenium

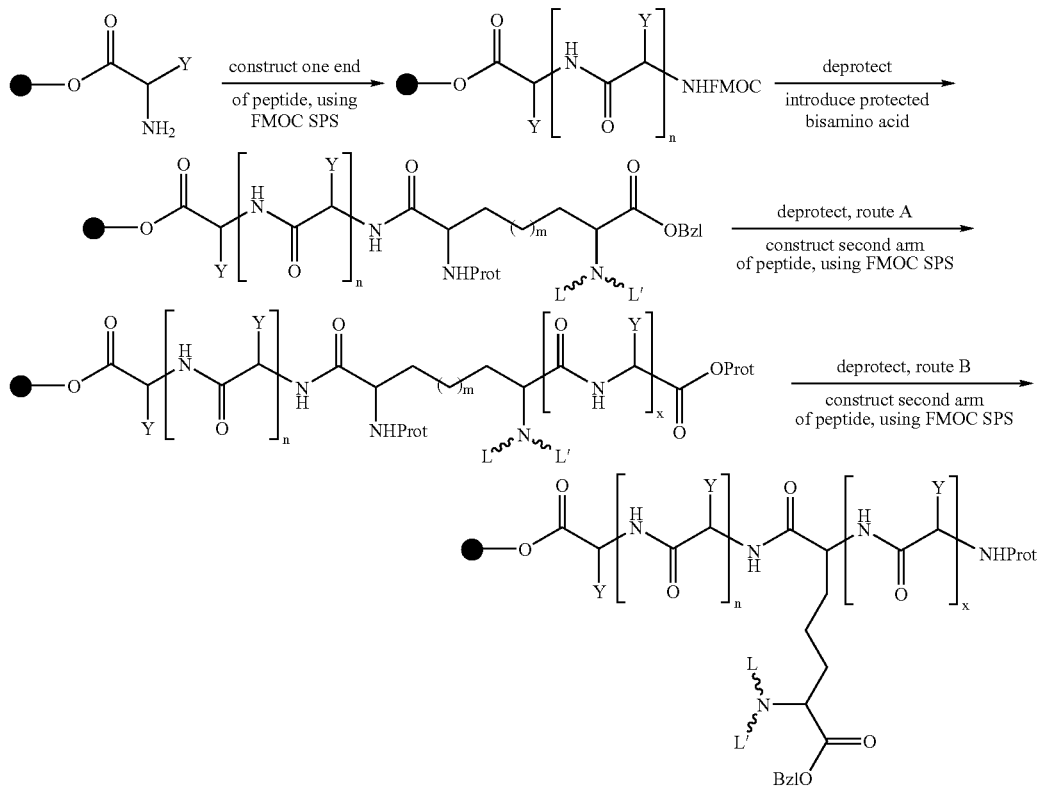

The bifunctional ligands L1a-L2d, L3a, L4a and L5a have been prepared and the for-MLF and for-NlcFNlcY peptide conjugates of L1a-L2d are currently under investigation.

Synthesis of Rhenium Analogs for Structural Characterization

Figure 3:
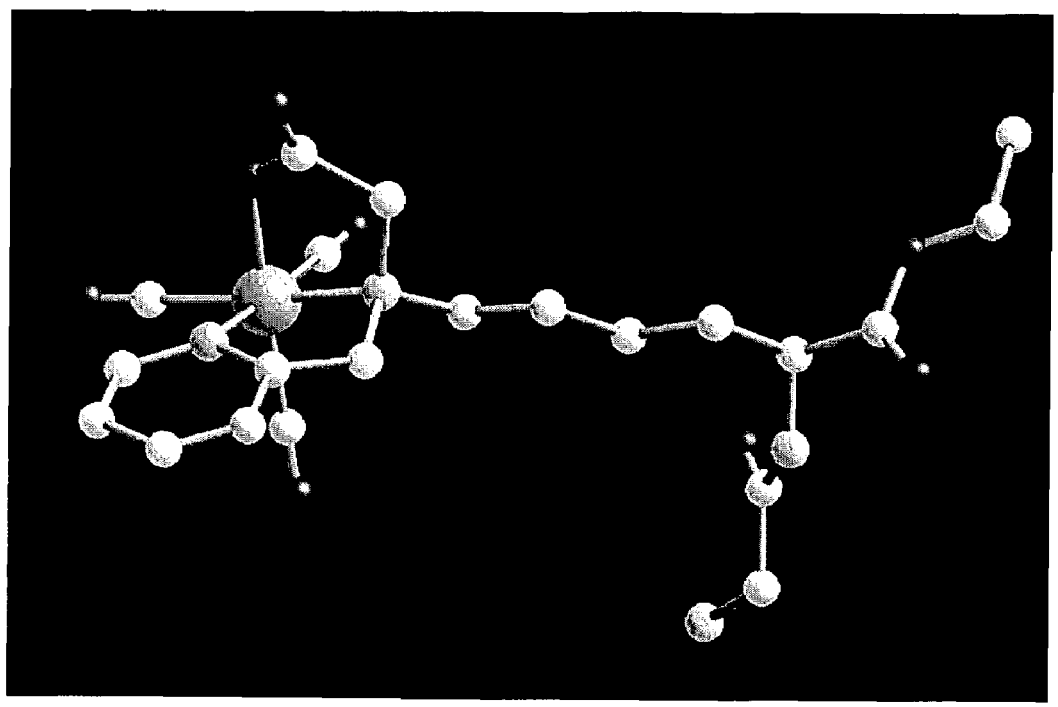
FIG. 3 depicts the structure of [Re(CO)$_3$(L1a-gly)].

Many of the properties of the Group VII metals technetium and rhenium are similar. It is anticipated that the metals will demonstrate similar reaction chemistry, which is often the case for the thiol, nitrogen, phosphine and oxo-chemistry of these two metals. Likewise, perrhenate and pertechnetate have very similar reaction behaviors. Rose, D. J., Maresca, K. P., Nicholson, T., Davison, A., Jones, A. G., Babich, J., Fischman, A., Graham, W., DeBord, J. R. D., Zubieta, J. "Synthesis and Characterization of Organohydrazine Complexes of Technetium, Rhenium, and Molybdenum with the {M($\eta$1-HxNNR)($\eta$2-HyNNR)} Core and Their Relationship to Radiolabeled Organohydrazine-Derivatized Chemotactic Peptides with Diagnostic Applications" Inorg. Chem. (1998) 37: 2701-2716. The similar reductions of the M(VII) oxo species by $SnCl_2$ allowed for easy substitution of the nonradioactive rhenium as a model for the medicinally complexes. Nicholson, T., Cook, J., Davison, A., Rose, D. J., Maresca K. P., Zubieta, J. A., Jones, A. G. "The synthesis and characterization of [MCl$_3$(N=NC$_5$H$_4$NH) (HN=NC$_5$H$_4$N)] from [MO$_4$]$^-$ (where M=Re, Tc) organodiazenido, organodiazene-chelate complexes" Inorg. Chim. Acta (1996) 252: 421-426. The coordination chemistry with {Re(CO)$_3$ (H$_2$O)$_3$}$^+$ has produced a number of derivatives including the model compound [Re(CO)$_3$(L1a-gly)] (4), shown in FIG. 3.

Re(V)-oxo Core

The synthesis of the rhenium analogs followed the established chemistry of the $N_2S_2$ system in forming stable, neutral, rhenium-oxo complexes. Davison A, Jones A G, Orvig C, et al: "A new class of oxotechnetium (5+) chelate complexes containing a TcON$_2$S$_2$ core" Inorg. Chem. 20: 1629-1631, 1981; Kung H F, Guo Y-Z, Mach R H, et al: "New Tc-99 complexes based on N$_2$S$_2$ ligands" J. Nucl. Med. 27: 1051, 1986 (abstr.); Kung H F, Molnar M, Billings J, et al: "Synthesis and biodistribution of neutral lipid-soluble Tc-99m complexes that cross the blood-brain barrier" J. Nucl. Med. 25: 326-332, 1984; and Kung H F, Yu C C, Billings J, et al: "Synthesis of new bis(aminoethanethiol) (BAT) derivatives: Possible ligands for $^{99m}$Tc brain imaging agents" J. Med. Chem. 28: 1280-1284, 1985. Our N$_3$ system, with three nitrogen donors forms a predictablable metal-complex with an overall net charge of zero. The synthesis of the Re(III) complexes was accomplished by reacting [TBA] [ReOBr$_4$(OPPh$_3$)] with the appropriate ligand in the ratio of 1:1.2 in 10 mL of methanol and three equivalents of NEt$_3$ as base. The reaction was allowed to reflux for roughly ½ hour. After cooling, the reaction products were be purified using a small column using the method established by Spies and co-workers. Spies, H., Fietz, T., Glaser, M., Pietzsch, H.-J., Johannsen, B. In "Technetium and Rhenium in Chemistry and Nuclear Medicine 3", Nicollini, M., Bandoli, G., Mazzi, U., eds., Padova, Italy, 1995, 4, 243. Alternatively, the rhenium (V) starting material [ReOCl$_3$(PPh$_3$)$_2$] may be employed as the potential rhenium starting material. This versatile material has proven successful in the past for dealing with nitrogen and sulfur donor atoms. Maresca, K. P., Femia, F. J., Bonavia, G. H., Babich, J. W., Zubieta, J. "Cationic comples of the '3+1' oxorhenium-thiolate complexes" Inorganic Chemistry Acta (2000) 297: 98-105; and Maresca, K. P., Rose, D. J., Zubieta, J. "Synthesis and charaterization of a binuclear rhenium nitropyrazole" Inorganica Chimica Acta (1997) 260: 83-88. The synthesized rhenium-DPMA complexes have been run through a HPLC column for separation and purification purposes following the procedures described for the technetium complexes. The complexes were then analyzed by elemental analysis, infrared spectroscopy, mass spectroscopy, and NMR spectroscopy.

Re(I)(CO)$_3$+ Core

The Re(I)(CO)3$^+$ system displays similar reaction chemistry to that of the Tc-99m tricarbonyl core. The use of [NEt$_4$]$_2$[ReBr$_3$(CO)$_3$], as the starting material leads to easy formation of the fac-Re(CO)$_3$(L)$_3$ core. The [NEt$_4$]$_2$[ReBr$_3$(CO)$_3$] is readily derived from the [ReBr(CO)$_5$]. The synthesis of the Re(I) complexes has been accomplished by reacting [NEt$_4$]$_2$[ReBr$_3$(CO)$_3$] with the appropriate DPMA ligand in the ratio of 1:1.2 in 10 mL of H$_2$O and three equivalents of NEt$_3$ as base. The reaction was allowed to heat at 80° C. for 4 hours. After cooling, the reaction products were purified using a small column using the method established by Alberto and coworkers. Spies, H., Fietz, T., Glaser, M., Pietzsch, H.-J., Johannsen, B. In "Technetium and Rhenium in Chemistry and Nuclear Medicine 3", Nicollini, M., Bandoli, G., Mazzi, U., eds., Padova, Italy, 1995, 4, 243. This versatile material has proven successful in the past for dealing with nitrogen and oxygen donor atoms. The synthesized rhenium-DPMA complexes were then run through a HPLC column for separation and purification purposes, following the procedures previously described for the technetium complexes. Next, the complexes were analyzed by: elemental analysis, infrared spectroscopy, mass spectroscopy, and NMR spectroscopy.

The stability and robustness of the technetium-di(pyridine) complexes was assessed using challenges with free cysteine and histidine. Specifically, the experiments were performed using [$^{99m}$Tc(CO)$_3$(dipyridinemethylamine)]$^{+1}$. The complex was found to be stable in the face of relatively high concentrations of these amino acids. For example, HPLC analyses showed no significant change in the components when an aqueous solution of the complex was incubated with cysteine for 18 hours at 37 C at pH 7.4.

We have also explored extensively the synthesis and use as ligands for metal tricarbonyls, e.g., Re and Tc tricarbonyls, protected and unprotected versions of [ε-{N,N-di(pyridyl-2-methyl)}α-(fmoc)lysine] (Fmoc-DpK). The choice of the tridentate DpK for the exploration of a single amino acid chelate was based on the excellent RCP and RCY, and the potential to prepare radiopharmaceutical kits. The pyridine-2-methylamine was easily derivatized into the amino acid. The biodistribution results showed [$^{99m}$Tc(CO)$_3$ (DpK)] having rapid blood clearance with % ID/g=0.6 at 5 minutes to % ID/g=0.07 by 30 minutes.

This approach enables the creation of libraries containing the {M(CO)$_3$}$^{1+}$ core. We have begun to define the biological fate of the $^{99m}$Tc-dipyridine complexes, allowing us to compare a series of future tridentate analogs. The dipyridine labeling proceeded in high yield and was stable to excess histidine and cysteine challenges for more than 18 hours. Biodistribution studies showed major accumulation in kidney and liver only, at early timepoints. Activity decreased in all tissues as a function of time, except in the GI tract, which increased with time. These experiments suggest that dipyridine is a potential enabling technology for the labeling of important biomolecules.

Definitions

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry,* McGraw Hill Book Company, New York, (1977 edition) pp. 251-259. The Hammett constant values are generally negative for electron donating groups (σ[P]=−0.66 for NH$_2$) and positive for electron withdrawing groups (σ[P]=0.78 for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., C$_1$-C$_{30}$ for straight chain, C$_3$-C$_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, azetidine, azepine, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle", as used herein, refers to an aromatic or non-aromatic ring in which each atom of the ring is carbon.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

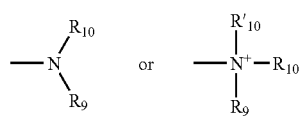

wherein R$_9$, R$_{10}$ and R'$_{10}$ each independently represent a group permitted by the rules of valence.

The term "acylamino" is art-recognized and refers to a moiety that can be represented by the general formula:

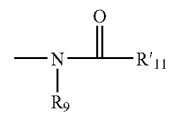

wherein R$_9$ is as defined above, and R'$_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

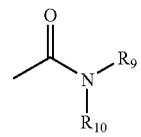

wherein R$_9$, R$_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

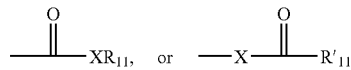

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

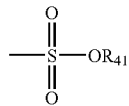

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemist of ordinary skill in the art appears in the first issue of each volume of the *Journal of Organic Chemistry;* this list is typically presented in a table entitled Standard List of Abbreviations. The abbreviations contained in said list, and all abbreviations utilized by organic chemist of ordinary skill in the art are hereby incorporated by reference.

The term "sulfate" is art recognized and includes a moiety that can be represented by the general formula:

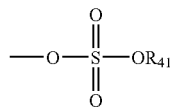

in which $R_{41}$ is as defined above.

The term "sulfonylamino" is art recognized and includes a moiety that can be represented by the general formula:

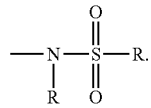

The term "sulfamoyl" is art-recognized and includes a moiety that can be represented by the general formula:

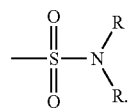

The term "sulfonyl", as used herein, refers to a moiety that can be represented by the general formula:

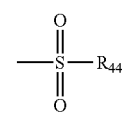

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

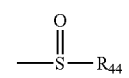

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, it may be isolated using chiral chromatography methods, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to opioid receptors. In general, the compounds of the present invention may be prepared by the methods illustrated in the general reaction schemes as, for example, described below, or by modifications thereof, using readily available starting materials, reagents and conventional synthesis procedures.

In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Compounds of the Invention

In certain embodiments, a compound of the present invention is represented by A:

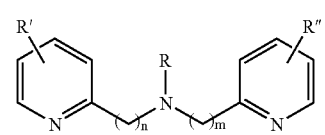

wherein

R represents H, alkyl, hydroxyalkyl, alkoxyalkyl, aminoalkyl, thioalkyl, alkenyl, alkynyl, aryl, heteroaryl, aralkyl, heteroaralkyl, acyl, aminoacyl, hydroxyacyl, thioacyl, —CO$_2$H, —(CH$_2$)$_d$—R$_{80}$, or an amino acid radical;

R' is absent or present from 1 to 4 times;

R" is absent or present from 1 to 4 times;

each instance of R' or R" is selected independently from the group consisting of halogen, alkyl, alkenyl, alkynyl, hydroxyl, alkoxyl, acyl, acyloxy, acylamino, silyloxy, amino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, cyano, guanidine, amidine, acetal, ketal, amine oxide, aryl, heteroaryl, aralkyl, heteroaralkyl, azido, aziridine, carbamoyl, epoxide, hydroxamic acid, imide, oxime, sulfonamide, thioamide, thiocarbamate, urea, thiourea, and —(CH$_2$)$_d$—R$_{80}$;

R$_{80}$ represents independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, peptide, saccharide, ribonucleic acid, (deoxy)ribonucleic acid, or ligand for a G-protein-coupled receptor;

d is an integer in the range 0 to 12 inclusive;

m is an integer in the range 0 to 6 inclusive; and n is an integer in the range 0 to 6 inclusive.

In certain embodiments, the compounds of the present invention are represented by A and the attendant definitions, wherein said compound is complexed with a radionuclide.

In certain embodiments, the compounds of the present invention are represented by A and the attendant definitions, wherein said compound is complexed with a radionuclide, wherein said radionuclide is technetium or rhenium.

In certain embodiments, the compounds of the present invention are represented by A and the attendant definitions, wherein m is 1.

In certain embodiments, the compounds of the present invention are represented by A and the attendant definitions, wherein n is 1.

In certain embodiments, the compounds of the present invention are represented by A and the attendant definitions, wherein m is 1; and n is 1.

In certain embodiments, the compounds of the present invention are represented by A and the attendant definitions, wherein R' is absent.

In certain embodiments, the compounds of the present invention are represented by A and the attendant definitions, wherein R" is absent.

In certain embodiments, the compounds of the present invention are represented by A and the attendant definitions, wherein R' is absent; and R" is absent.

In certain embodiments, the compounds of the present invention are represented by A and the attendant definitions, wherein m is 1; n is 1; R' is absent; and R" is absent.

In certain embodiments, the compounds of the present invention are represented by A and the attendant definitions, wherein R is —(CH$_2$)$_d$—R$_{80}$.

In certain embodiments, the compounds of the present invention are represented by A and the attendant definitions, wherein m is 1; n is 1; R' is absent; R" is absent; and R is —(CH$_2$)$_d$—R$_{80}$.

In certain embodiments, the compounds of the present invention are represented by A and the attendant definitions, wherein m is 1; n is 1; R' is absent; R" is absent; and R is —(CH$_2$)$_d$—R$_{80}$; wherein said compound is complexed with a radionuclide.

In certain embodiments, the compounds of the present invention are represented by A and the attendant definitions, wherein m is 1; n is 1; R' is absent; R" is absent; and R is —(CH$_2$)$_d$—R$_{80}$; wherein said compound is complexed with a radionuclide, wherein said radionuclide is technetium or rhenium.

In certain embodiments, the compounds of the present invention are represented by A and the attendant definitions, wherein R is an amino acid radical.

In certain embodiments, the compounds of the present invention are represented by A and the attendant definitions, wherein R is an amino acid radical; m is 1; and n is 1.

In certain embodiments, the compounds of the present invention are represented by A and the attendant definitions, wherein R is an amino acid radical; m is 1; n is 1; R' is absent; and R" is absent.

In certain embodiments, the compounds of the present invention are represented by A and the attendant definitions, wherein R is an amino acid radical; m is 1; n is 1; R' is absent; and R" is absent; wherein said compound is complexed with a radionuclide.

In certain embodiments, the compounds of the present invention are represented by A and the attendant definitions, wherein R is an amino acid radical; m is 1; n is 1; R' is absent; and R" is absent; wherein said compound is complexed with a radionuclide, wherein said radionuclide is technetium or rhenium.

In certain embodiments, a compound of the present invention is represented by B:

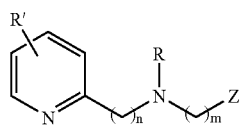

B wherein

Z represents thioalkyl, carboxylate, 2-(carboxy)aryl, 2-(carboxy)heteroaryl, 2-(hydroxy)aryl, 2-(hydroxy)heteroaryl, 2-(thiol)aryl, or 2-(thiol)heteroaryl;

R represents H, alkyl, hydroxyalkyl, alkoxyalkyl, aminoalkyl, thioalkyl, alkenyl, alkynyl, aryl, heteroaryl, aralkyl, heteroaralkyl, acyl, aminoacyl, hydroxyacyl, thioacyl, —CO$_2$H, —(CH$_2$)$_d$—R$_{80}$, or an amino acid radical;

R' is absent or present from 1 to 4 times;

each instance of R' is selected independently from the group consisting of halogen, alkyl, alkenyl, alkynyl, hydroxyl, alkoxyl, acyl, acyloxy, acylamino, silyloxy, amino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, cyano, guanidine, amidine, acetal, ketal, amine oxide, aryl, heteroaryl, aralkyl, heteroaralkyl, azido, aziridine, carbamoyl, epoxide, hydroxamic acid, imide, oxime, sulfonamide, thioamide, thiocarbamate, urea, thiourea, and —(CH$_2$)$_d$—R$_{80}$;

R$_{80}$ represents independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, peptide, saccharide, ribonucleic acid, (deoxy)ribonucleic acid, or ligand for a G-protein-coupled receptor;

d is an integer in the range 0 to 12 inclusive;

m is an integer in the range 0 to 6 inclusive; and n is an integer in the range 0 to 6 inclusive.

In certain embodiments, the compounds of the present invention are represented by B and the attendant definitions, wherein said compound is complexed with a radionuclide.

In certain embodiments, the compounds of the present invention are represented by B and the attendant definitions, wherein said compound is complexed with a radionuclide, wherein said radionuclide is technetium or rhenium.

In certain embodiments, the compounds of the present invention are represented by B and the attendant definitions, wherein Z is carboxylate.

In certain embodiments, the compounds of the present invention are represented by B and the attendant definitions, wherein m is 1.

In certain embodiments, the compounds of the present invention are represented by B and the attendant definitions, wherein n is 1.

In certain embodiments, the compounds of the present invention are represented by B and the attendant definitions, wherein m is 1; and n is 1.

In certain embodiments, the compounds of the present invention are represented by B and the attendant definitions, wherein Z is carboxylate; m is 1; and n is 1.

In certain embodiments, the compounds of the present invention are represented by B and the attendant definitions, wherein R' is absent.

In certain embodiments, the compounds of the present invention are represented by B and the attendant definitions, wherein Z is carboxylate; m is 1; n is 1; and R' is absent.

In certain embodiments, the compounds of the present invention are represented by B and the attendant definitions, wherein R is —(CH$_2$)$_d$—R$_{80}$.

In certain embodiments, the compounds of the present invention are represented by B and the attendant definitions, wherein Z is carboxylate; m is 1; n is 1; R' is absent; and R is —(CH$_2$)$_d$—R$_{80}$.

In certain embodiments, the compounds of the present invention are represented by B and the attendant definitions, wherein Z is carboxylate; m is 1; n is 1; R' is absent; and R is —(CH$_2$)$_d$—R$_{80}$; wherein said compound is complexed with a radionuclide.

In certain embodiments, the compounds of the present invention are represented by B and the attendant definitions, wherein Z is carboxylate; m is 1; n is 1; R' is absent; and R is —$(CH_2)_d$—$R_{80}$; wherein said compound is complexed with a radionuclide, wherein said radionuclide is technetium or rhenium.

In certain embodiments, the compounds of the present invention are represented by B and the attendant definitions, wherein R is an amino acid radical.

In certain embodiments, the compounds of the present invention are represented by B and the attendant definitions, wherein R is an amino acid radical; m is 1; and n is 1.

In certain embodiments, the compounds of the present invention are represented by B and the attendant definitions, wherein R is an amino acid radical; m is 1; n is 1; and R' is absent.

In certain embodiments, the compounds of the present invention are represented by B and the attendant definitions, wherein R is an amino acid radical; m is 1; n is 1; and R' is absent; wherein said compound is complexed with a radionuclide.

In certain embodiments, the compounds of the present invention are represented by B and the attendant definitions, wherein R is an amino acid radical; m is 1; n is 1; and R' is absent; wherein said compound is complexed with a radionuclide, wherein said radionuclide is technetium or rhenium.

In certain embodiments, a compound of the present invention is represented by C:

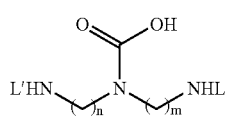

C wherein

L and L' represent independently for each occurrence 2-methylenepyridyl, methylenecarboxylate, alkyl, aryl, or aralkyl, wherein at least one of L or L' is methylenecarboxylate or 2-methylenepyridyl, and wherein the 2-methylenepyridyl may be unsubstituted on the ring or substituted with 1 to 4 instances of R';

R' is selected independently for each occurrence from the group consisting of halogen, alkyl, alkenyl, alkynyl, hydroxyl, alkoxyl, acyl, acyloxy, acylamino, silyloxy, amino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, cyano, guanidine, amidine, acetal, ketal, amine oxide, aryl, heteroaryl, aralkyl, heteroaralkyl, azido, aziridine, carbamoyl, epoxide, hydroxamic acid, imide, oxime, sulfonamide, thioamide, thiocarbamate, urea, thiourea, and —$(CH_2)_d$—$R_{80}$;

$R_{80}$ represents independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, peptide, saccharide, ribonucleic acid, (deoxy)ribonucleic acid, or ligand for a G-protein-coupled receptor;

d is an integer in the range 0 to 12 inclusive;

m is an integer in the range 0 to 6 inclusive; and n is an integer in the range 0 to 6 inclusive.

In certain embodiments, the compounds of the present invention are represented by C and the attendant definitions, wherein said compound is complexed with a radionuclide.

In certain embodiments, the compounds of the present invention are represented by C and the attendant definitions, wherein said compound is complexed with a radionuclide, wherein said radionuclide is technetium or rhenium.

In certain embodiments, the compounds of the present invention are represented by C and the attendant definitions, wherein L is methylenecarboxylate; and L' is alkyl.

In certain embodiments, the compounds of the present invention are represented by C and the attendant definitions, wherein L is 2-methylenepyridyl; and L' is alkyl.

In certain embodiments, the compounds of the present invention are represented by C and the attendant definitions, wherein L is alkyl; and L' is 2-methylenepyridyl.

In certain embodiments, the present invention relates to a formulation, comprising a compound represented by A, B, or C and the attendant definitions; and a pharmaceutically acceptable excipient.

The novel ligands described above, may be incorporated into radionuclide complexes used as radiographic imaging agents. Further, these ligands or complexes can be covalently or non-covalently attached to biologically active carrier molecules, such as, antibodies, enzymes, peptides peptidomimetics, hormones, and the like. The complexes of the present invention are prepared by reacting one of the aforementioned ligands with a radionuclide containing solution under radionuclide complex forming reaction conditions. In particular, if a technetium agent is desired, the reaction is carried out with a pertechnetate solution under technetium-99m complex forming reaction conditions. The solvent may then be removed by any appropriate means, such as evaporation. The complexes are then prepared for administration to the patient by dissolution or suspension in a pharmaceutically acceptable vehicle.

The present invention also relates to imaging agents containing a radionuclide complex as described above, in an amount sufficient for imaging, together with a pharmaceutically acceptable radiological vehicle. The radiological vehicle should be suitable for injection or aspiration, such as human serum albumin; aqueous buffer solutions, e.g tris (hydromethyl) aminomethane (and its salts), phosphate, citrate, bicarbonate, etc; sterile water; physiological saline; and balanced ionic solutions containing chloride and or dicarbonate salts or normal blood plasma cations such as calcium, potassium, sodium, and magnesium.

The concentration of the imaging agent according to the present invention in the radiological vehicle should be sufficient to provide satisfactory imaging, for example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera. In certain embodiments, the present invention relates to a method of imaging a region in a patient, comprising the steps of: administering to a patient a diagnostically effective amount of a compound of the present invention complexed with a radionuclide; exposing a region of said patient to radiation; and obtaining an image of said region of said patient. In certain embodiments of the method of imaging a region in a patient, said region of said patient is the head or thorax.

Pharmaceutical Formulations

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Formulations of the present invention may be based in part on liposomes. Liposomes consist of a phospholipid bilayer which forms a shell around an aqueous core. Methods for preparing liposomes for administration to a patient are known to those skilled in the art; for example, U.S. Pat. No. 4,798,734 describes methods for encapsulation of biological materials in liposomes. The biological material is dissolved in a aqueous solution, and the appropriate phospholipids and lipids are added, along with surfactants if required. The material is then dialyzed or sonicated, as necessary. A review of known methods is presented by G. Gregoriadis, Chapter 14 ("Liposomes"), in Drug Carriers in Biology and Medicine, pp. 287-341 (Academic Press, 1979).

Formulations of the present invention may be based in part on polymeric microparticles. Microspheres formed of polymers or proteins are also well known to those skilled in the art, and can be tailored for passage through the gastrointestinal tract, as described in U.S. Pat. Nos. 4,906,474, 4,925,673, and 3,625,214, for example. There are a number of well-known methods, including solvent evaporation and coacervation/phase separation, for preparing microspheres. Bioerodible microspheres can be prepared using any of the methods developed for making microspheres for drug delivery, as described, for example, by Mathiowitz et al., J. Appl. Polymer Sci. 35, 755-774(1988), and P. Deasy, in Microencapsulation and Related Drug Processes, pp. 61-193, (Dekker, 1984), the teachings of which are incorporated herein. The selection of a method depends on the drug properties and choice of polymer, as well as the size, external morphology, and degree of crystallinity desired, as discussed, for example, by Benita et al., J. Pharm. Sci. 73, 1721-1724 (1984), Jalil and Nixon, J. Microencapsulation, 7, 297-325 (1990), and Mathiowitz et al., Scanning Microscopy 4, 329-340(1990), the teachings of which are incorporated herein.

In solvent evaporation, described, for example, in Mathiowitz et al., (1990), Benita, and U.S. Pat. No. 4,272,398 to Jaffe, the polymer is dissolved in a volatile organic solvent. The drug, either in soluble or particulate form, is added to the polymer solution and the mixture is suspended in an aqueous phase containing a surface active agent such as poly(vinyl alcohol). The resulting emulsion is stirred until most of the organic solvent evaporates, leaving solid microspheres. Microspheres of various sizes (1-1000 microns) and morphologies may be obtained by this method, which is useful for non-labile polymers.

Coacervation/phase separation techniques have been used to encapsulate both solid and liquid core materials with various polymer coatings. U.S. Pat. Nos. 2,730,456, 2,730,457, and 2,800,457 to Green and Schleichter, describe gelatin and gelatin-acacia (gum arabic) coating systems, for example. Simple coacervation employs a single colloid (e.g. gelatin in water) and involves the removal of the associated water from around the dispersed colloid by agents with a higher affinity for water, such as alcohols and salts. Complex coacervation employs more than one colloid, and the separation proceeds mainly by charge neutralization of the colloids carrying opposite charges rather than by dehydration. Coacervation may also be induced using nonaqueous vehicles, as described in Nakano et al., Int. J. Pharm, 4, 29-298(1980), for example.

Hydrogel microspheres made of gel-type polymers such as alginate or polyphosphazenes or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as illustrated, for example, by Salib, et al., Pharmazeutische Industrie 40-11A, 1230(1978), the teachings of which are incorporated herein. The advantage of this system is the ability to further modify the surface of the microspheres by coating them with polycationic polymers (such as polylysine) after fabrication, as described, for example, by Lim et al, J. Pharm Sci. 70, 351-354(1981). The microsphere particle size depends upon the extruder size as well as the polymer and gas flow rates.

Examples of polymers that can be used include polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

A diluent used in a composition of the present invention can be one or more compounds which are capable of densifying the active principle to give the desired mass. The preferred diluents are mineral phosphates such as calcium phosphates; sugars such as hydrated or anhydrous lactose, or mannitol; and cellulose or cellulose derivatives, for example microcrystalline cellulose, starch, corn starch or pregelatinized starch. Very particularly preferred diluents are lactose monohydrate, mannitol, microcrystalline cellulose and corn starch, used by themselves or in a mixture, for example a mixture of lactose monohydrate and corn starch or a mixture of lactose monohydrate, corn starch and microcrystalline cellulose.

A binder employed in a composition of the present invention can be one or more compounds which are capable of densifying a compound of formula (I), converting it to coarser and denser particles with better flow properties. The preferred binders are alginic acid or sodium alginate; cellulose and cellulose derivatives such as sodium carboxymethyl cellulose, ethyl cellulose, hydroxyethyl cellulose, hydroxypropyl cellulose, hydroxypropyl methyl cellulose or methyl cellulose, gelatin; acrylic acid polymers; and povidone, for example povidone K-30; hydroxypropyl methyl cellulose and povidone K-30 are very particularly preferred binders.

A disintegrating agent employed in a composition of the present invention can be one or more compounds which facilitate the disintegration of the prepared formulation when it is placed in an aqueous medium. The preferred disintegrating agents are cellulose or cellulose derivatives such as sodium carboxymethyl cellulose, crosslinked sodium carboxymethyl cellulose, micro-crystalline cellulose, cellulose powder, crospovidone; pregelatinized starch, sodium starch glyconate, sodium carboxymethyl starch, or starch. Crospovidone, crosslinked sodium carboxymethyl cellulose and sodium carboxymethyl starch are preferred disintegrating agents.

An antiadhesive employed in a composition of the present invention can be one or more compounds which are capable of reducing the sticky character of the formulation, for example of preventing adhesion to metal surfaces. The preferred antiadhesives are compounds containing silicon, for example silica or talcum.

A flow promoter employed in a composition of the present invention can be one or more compounds which are capable of facilitating the flow of the prepared formulation. The preferred flow promoters are compounds containing silicon, for example anhydrous colloidal silica or precipitated silica.

A lubricant employed in a composition of the present invention can be one or more compounds which are capable of preventing the problems associated with the preparation of dry forms, such as the sticking and/or seizing problems which occur in the machines during compression or filling. The preferred lubricants are fatty acids or fatty acid derivatives such as calcium stearate, glyceryl monostearate, glyceryl palmitostearate, magnesium stearate, sodium laurylsulfate, sodium stearylfumarate, zinc stearate or stearic acid; hydrogenated vegetable oils, for example hydrogenated castor oil; polyalkylene glycols or polyethylene glycol; sodium benzoate; or talcum. Magnesium stearate or sodium stearylfumarate is preferred according to the present invention.

A color employed in a formulation of the present invention can be one or more compounds which are capable of imparting the desired color to the prepared formulation. The addition of a color can serve for example to differentiate between formulations containing different doses of active principle. The preferred colors are iron oxides.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in silu in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Combinatorial Libraries

The subject compounds readily lend themselves to the creation of combinatorial libraries for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116: 2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998-4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c. f., Bray et al. (1990) Tetrahedron Lett 31:5811-5814; Valerio et al. (1991) Anal Biochem 197:168-177; Bray et al. (1991) Tetrahedron Lett 32:6163-6166).

C) Divide-Couple-Recombine

In yet another embodiment, a variegated library of compounds can be provided on a set of beads utilizing the strategy of divide-couple-recombine (see, e.g., Houghten (1985) PNAS 82:5131-5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) PNAS 82:5131-5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) Annu Rep Med Chem 26:271-280; Fodor, S. P. A. (1991) Science 251:767; Pirrung et al. (1992) U.S. Pat. No. 5,143,854; Jacobs et al. (1994) Trends Biotechnol 12:19-26). The spatial resolution of photolithography affords miniaturization. This technique can be carried out through the use of protection/deprotection reactions with photolabile protecting groups.

The key points of this technology are illustrated in Gallop et al. (1994) J Med Chem 37:1233-1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381-5383), and an example of such a library appeared the following year (Needles et al. (1993) PNAS 90:10700-10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) J Am Chem Soc 115:2529-2531), orthogonality in synthesis is achieved by employing acid-labile protection for the coding strand and base-labile protection for the compound strand.

In an alternative approach (Nikolaiev et al. (1993) Pept Res 6:161-170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) Tetrahedron Lett 32:3891-3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) PNAS 90:10922-10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) J Org Chem 59:4723-4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027-6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Exemplification

The invention now being generally described, it will be more readily understood by reference to the following examples, which are included merely for purposes of illustration of certain aspects and embodiments of the present invention, and are not intended to limit the invention.

EXAMPLE 1

Synthesis of $(C_5H_4NCH_2)_2NH$

In a 100 mL round bottomed flask was placed 2-aminomethylpyridine (2.50 g, 0.023 moles). The system was placed under nitrogen. The solid was dissolved in 20 mL of acetonitrile followed by the addition of 7 mL of triethylamine. Next the 2-bromomethylpyridine hydrobromide (5.80 g, 0.023 moles) was added. The reaction mixture was allowed to stir for 0.5 hours at 55 C., whereupon the reaction was vacuumed down to residue. The mixture was purified using a large silica column (10% methanol/methylene chloride). $^1$H NMR (CDCl$_3$, ppm): 2.97 (s, H), 3.98 (s, 4H), 7.15 (m, 2H), 7.28 (m, 2H), 7.65 (m, 2H), 8.55 (m, 2H). Mass Spectroscopy demonstrated the molecular weight to be 199.

EXAMPLE 2

Synthesis of $(C_5H_4NCH_2)_3N$

In a 100 mL round bottomed flask was placed 2-aminomethylpyridine (2.50 g, 0.023 moles). The system was placed under nitrogen. The solid was dissolved in 20 mL of acetonitrile followed by the addition of 7 mL of triethylamine. Next the 2-bromomethylpyridine hydrobromide (5.80 g, 0.023 moles) was added. The reaction mixture was allowed to stir for 0.5 hours at 55 C., whereupon the reaction was vacuumed down to residue. The mixture was purified using a large silica column (10% methanol/methylene chloride). $^1$H NMR (CDCl$_3$, ppm): 3.98 (s, 4H), 7.15 (m, 2H), 7.55 (m, 2H), 7.65 (m, 2H), 8.55 (m, 2H). Mass Spectroscopy demonstrated the molecular weight to be 291 (M+1).

EXAMPLE 3

Synthesis of $(C_5H_4NCH_2)_2NCH_3$

In a 100 mL round bottomed flask was placed dipyridinemethylamine DPMA (1.00 g, 5.03 mmoles). The solid was dissolved in 10 mL of acetonitrile followed by the addition of 2 mL of dimethylformamide. Next the methyliodide (0.637 g, 4.52 mmoles) was added. The reaction mixture was allowed to stir for 0.5 hours at room temperature, whereupon the reaction was vacuumed down to residue. The mixture was purified using a large silica column (10% methanol/methylene chloride). $^1$H NMR (CDCl$_3$, ppm): 2.19 (s, 3H), 3.85 (s, 4H), 7.15 (m, 2H), 7.50 (d, 2H), 7.65 (m, 2H), 8.55 (d, 2H). Mass Spectroscopy demonstrated the molecular weight to be 214 (M+1).

EXAMPLE 4

Synthesis of $(C_5H_4NCH_2NCH_2COOH)$ $\{CH_2CH_2CH_2N(CH_3)_3\}$

In a 100 mL round bottomed flask was placed pyridinemethylamine monoacetic acid (PAMA) (0.30 g, 1.55 mmoles). The solid was dissolved in 10 mL of acetonitrile followed by the addition of 5 mL of dimethylformamide. Next, two equivalents of the iodine salt of 1-chloropropyltrimethylamine (0.815 g, 3.10 mmoles) was added. Finally, potassium carbonate (0.10 g, 0.724 mmol) was added. The reaction mixture was heated at 130° C. for 3 hours, whereupon the reaction was vacuumed down to residue. The mixture was purified using a reverse phase C18 column (99% H$_2$O/1% CH$_3$CN). $^1$H NMR (CDCl$_3$, ppm): 2.20 (s, 2H), 3.05 (s, 2H), 3.14 7 (s, 9H), 3.34 (m, 2H), 4.28 (s, 2H), 7.60 (d, 2H), 7.70 (d, 2H), 8.1 (d, 2H), 8.65 (d, 2H).

EXAMPLE 5

Synthesis of $(C_5H_4NCH_2NCH_2COOH)(CH_2(CH_2)_{10}COOH)$

This compound was prepared using the same synthetic protocol as in the synthesis of $(C_5H_4NCH_2NCH_2COOH)\{CH_2CH_2Ch_2N(CH_3)_3\}$. See Example 4. $^1$H NMR CDCl$_3$, ppm): 1.25 (m, 10H), 1.45 (s, 2H), 1.60 (s, 2H), 1.75 (m, 2H), 2.3 (m, 2H), 2.55 (m, 2H), 3.63 (s, 3H), 3.80 (s, 2H), 7.05 (dd, 2H), 7.55 (d, 2H), 7.65 (dd, 2H), 8.53 (d, 2H).

EXAMPLE 6

Synthesis of $(C_5H_4NCH_2)_2N(CH_2COOCH_2CH_3)$

This compound was prepared using the same synthetic protocol as in the synthesis of $(C_5H_4NCH_2NCH_2COOH)\{(CH_2CH_2CH_2N(CH_3)_3)\}$. See Example 4. However, DPMA was used in place of PAMA. $^1$H NMR (CDCl$_3$, ppm): 1.25 (t, 3H), 3.45 (s, 2H), 3.95 (s, 4H), 4.15 (q, 2H), 7.1 (m, 2H), 7.55 (m, 4H), 8.53 (s, 2H).

EXAMPLE 7

(Bis(2-pyridylmethyl)amino)acetic Acid

2-Chloromethylpyridine hydrochloride (9.2 g, 8.53 mmol) and glycin (2 g, 26.6 mmol) were dissolved in water (30 mL) and stirred at room temperature for five days, with addition of 5 mol aqueous NaOH solution at intervals to maintain the pH at 8-10. The resulting dark red solution was extracted with ethyl acetate, neutralized with HCl and concentrated. The residue was dissolved in dichloromethane, and the insoluble sodium chloride was filtered. Pale yellow crystals formed from the filtrate, which were collected and dried under vacuum. Yield (2.87 g) (11.2 mmol, 42%). $^1$H NMR (CDCl$_3$), 300 MHz): 3.39 (s, 2H), 3.98 (s, 4H), 7.06

(t, 2H), 7.30 (d, 2h), 7.56 (t, 2H), 8.36 (d, 2H). $^{13}$C NMR (CD$_3$OD, 300 MHz): 57.36 (C, CH$_2$), 59.77 (2C, PyCH$_2$), 124.77 (2CH, Py), 125.15 (2CH, Py), 139.00 (C, CH$_2$), 149.76 (2CH, Py), 156.10 (2C, Py), 173.05 (C, CO$_2$H).

EXAMPLE 8

(Bis(2-pyridylmethyl)amino)propionic Acid

This compound was synthesized by a similar procedure as described as above, except that 3-aminopropionic acid was used instead of glycine. The product was collected as pale red crystals from dichloromethane. Yield (2.74 g, 10.1 mmol, 45%). $^1$H NMR (CDCl$_3$), 300 MHz): 2.64 (t, 2H), 3.03 (t, 2H), 3.95 (s, 4H), 7.21 (t, 2H), 7.38 (d, 2H), 8.55 (t, 2H), 8.66 (d, 2H). $^{13}$C NMR (CD$_3$OD, 300 MHz): 33.15 (C, CH$_2$), 51.90 (C, NCH$_2$), 60.22 (2C, PyCH$_2$), 124.37 (2CH, Py), 125.29 (2CH, Py), 138.98 (2C, Py), 149.72 (2CH, Py), 158.50 (2C, Py), 176.79 (C, CO$_2$H).

EXAMPLE 9

Ethyl-(bis(2-pyridylmethyl)amino)acetate (Bis(2-pyridylmethyl)amino)acetic acid (1 g, 3.89 mmol) was taken in saturated ethanolic HCl (20 mL) and refluxed for 3 h. The reaction mixture was quenched with triethylamine and concentrated. The residue was dissolved in dichloromethane, washed with water, dried (Na2SO4) and concentrated. The residue was purified on silica gel column chromatography using methanol:chloroform (3:97) to give Ethyl-(bis(2-pyridylmethyl)amino)acetate as viscous liquid. Yield (0.910 g, 3.19 mmol, 82%). $^1$H NMR (CDCl$_3$), 300 MHz): 1.22 (t, 2H), 3.42 (s, 2H), 3.97 (s, 4H), 4.12 (q, 2H), 7.12 (t, 2H), 7.53 (d, 2H), 7.62 (t, 2H), 8.49 (d, 2H). $^{13}$C NMR (CD$_3$OD, 300 MHz): 13.99 (C, CH$_3$), 54.67 (C, CH$_2$), 59.70 (2C, PyCH$_2$), 60.21 (2C, OCH$_2$), 121.88 (2CH, Py), 122.93 (2CH, Py), 136.32 (2CH, Py), 148.80 (2CH, Py), 158.80 (2C, Py), 171.05 (C, CO$_2$H).

EXAMPLE 10

Ethyl-(bis(2-pyridylmethyl)amino)propionate

This compound was synthesized by a similar procedure as described above, except that (Bis(2-pyridylmethyl)amino) propionic acid was used instead of (Bis(2-pyridylmethyl) amino)acetic acid. The product was collected as a viscous liquid. Yield (1.37 g, 4.59 mmol, 83%). $^1$H NMR (CDCl$_3$), 300 MHz): 1.09 (t, 3H), 2.45 (t, 2H), 2.84 (t, 2H), 3.74 (s, 4H), 3.98 (q, 2H), 7.03 (t, 2H), 7.39 (d, 2H), 7.51 (t, 2H), 8.48 (d, 2H). $^{13}$C NMR (CD$_3$OD, 300 MHz): 13.70 (C, CH$_3$), 32.22 (C, CH$_2$) 49.39 (C, NCH$_2$), 59.45 (2C, PyCH$_2$), 59.55 (C, OCH$_2$), 121.47 (2CH, Py), 122.42 (2CH, Py), 135.82 (2CH, Py), 148.40 (2CH, Py), 158.91 (2C, Py), 171.74 (C, CO$_2$H).

EXAMPLE 11

Synthesis of N-α-(tert-Butoxycarbonyl)-N-ω-bis(2-pyridylmethyl)-L-lysine (L1c-Boc)

2-Chloromethylpyridine hydrochloride (1.4 g, 8.53 mmol) and N-α-(tert-Butoxycarbonyl)-L-lysine (1 g, 4.06 mmol) were dissolved in water and stirred at room temperature for five days, with addition of 5 mol dm$^{-3}$ aqueous NaOH solution at intervals to maintain the pH at 8-10. The resulting dark red solution was extracted with ethyl acetate, and then the aqueous phase was acidified to pH 3-4 by 1 mol dm$^{-3}$ HCl and extracted with Chloroform and concentrated. This residue purified by column chromatography using 10% chloroform in methanol to give N-α-(tert-Butoxycarbonyl)-N-ω-bis(2-pyridylmethyl)-L-lysine (950 mg, 55%). $^1$H NMR (CDCl$_3$), 300 MHz): 1.41 (s, 9H), 1.26-1.62 (m, 6 H), 2.58 (t, 2H), 3.84 (s, 4H), 4.24 (t, H), 7.15 (m, 2H), 7.48 (d, 2H), 7.65 (m, 2H), 8.53 (d, 2H). $^{13}$C NMR (CD$_3$OD, 300 MHz): 24.31 (C, CH$_2$), 26.66 (C, CH$_2$), 28.93 (3C, t-Bu), 33.15 (C, CH$_2$), 55.50 (C, NCH$_2$), 60.12 (2C, PyCH$_2$), 80.06 (C, NCH) 124.34 (2C, Py), 125.11 (2CH, Py), 138.93 (2CH, Py), 149.72 (2CH, Py), 157.71 (2C, Py), 177.49 (C, CO$_2$H).

EXAMPLE 12

Synthesis of N-α-(2-pyridylmethyl)-N-ω-(tert-Butoxycarbonyl)-L-lysine (L2d-Boc)

2-Chloromethylpyridine hydrochloride (730 mg, 4.46 mmol) and N-α-(tert-Butoxycarbonyl)-L-lysine (1 g, 4.06 mmol) were dissolved in water and stirred at room temperature for two days, with addition of 5 mol dm$^{-3}$ aqueous NaOH solution at intervals to maintain the pH at 8-10. The resulting dark red solution was extracted with ethyl acetate, and then the aqueous phase was acidified to pH 6 by 1 mol dm$^{-3}$ HCl and followed by treating with chloroform the required product precipitate out, which was filtered and dried under vacuum (670 mg, 49%).

EXAMPLE 13

Labeling the DPMA Analogs with Tc-99m using Labeling Methods Based on the Tc(V)-oxo and Tc(I)(CO)$_3$L$_3$ Cores Tc(V)-oxo Core Preparation of the Tc-99m-labeled DPMA derivatives was achieved by adding 10 mCi of TcO$_4^-$ to a 0.9% saline solution of the DPMA derivative (200 mg/3 mL). The mixture was heated at 80° C. for 30 min. Depending on the biological ligand, the solution was used as needed or the mixture was extracted with ethyl acetate (3, 1 mL portions), dried over sodium sulfate, and dried under N$_2$. The residue was then re-dissolved in ethanol (400 uL) and purity checked via HPLC by a Vydac C18 (5 mm, 25 cm) column using methanol to elute the reaction products.

Tc(I)(CO)$_3$+ Core

The Tc(I) carbonyl chemistry allows for the possibility of an alternative route to form stable $^{99m}$Tc-DPMA complexes. To explore this labeling method we began by placing Na$_2$CO$_3$ (0.004 g, 0.038 mmol), NaBH$_4$ (0.005 g, 0.13 mmol), and 2 mg of the DPMA derivative in a vial. Next, the vial was sealed and flushed with CO for 10 min. To the vial was added 1 mL of Na $^{99m}$TcO$_4^-$ in saline. Finally the solution was heated to 100° C. for 30 minutes. After cooling, the reaction was then checked for purity via HPLC by a Vydac C18 (5 mm, 25 cm) column using methanol to elute the reaction products.

Alternatively, a 'two pot' synthesis could be performed, where the DPMA derivative was added after the formation of [$^{99m}$Tc(OH$_2$)$_3$(CO)$_3$]$^+$. After cooling, 0.3 mL of 1 M PBS solution was added (pH 7.4), resulting in the stable formation of [$^{99m}$Tc(OH$_2$)$_3$(CO)$_3$]$^+$. This Tc(I) tricarbonyl species was then heated at 75° C. for 30 minutes with the DPMA derivative to form the $^{99m}$Tc-DPMA complex. The reaction was then checked for purity via HPLC by a Vydac C18 (5 mm, 25 cm) column using methanol to elute the reaction products. The versatility of the reaction allows for the reaction of a variety of sensitive biological DPMA derivatized ligands to be kept under idealized conditions.

EXAMPLE 14

Synthesis of $ReCl_3\{(C_5H_4NCH_2)_2N(CH_2COOCH_2CH_3)\}$

To a solution of $[ReOCl_3(PPh_3)_2]$ (0.0822 g, 0.0986 mmol) in 1 mL of chloroform was added dropwise a solution of excess dipyridinemethylamine ethyl acetate in 1 mL of chloroform. The solution remained olive green until the addition of triethylamine (0.08 mL, 0.574 mmol) whereupon it immediately changed from olive to forest green with precipitation of the product. The solution was stirred for an additional 30 minutes and then evaporated to dryness. X-ray quality crystals were grown by slow diffusion of pentane into a solution of the compound in methylene chloride. $^1H$ NMR ($CDCl_3$, ppm): 1.25 (t, 3H), 3.45 (s, 2H), 3.95 (s, 4H), 4.15 (q, 2H), 7.1 (m, 2H), 7.55 (m, 4H), 8.53 (s, 2H).

EXAMPLE 15

Synthesis of $ReCO_2\{(C_5H_4NCH_2)_2NH_2)Br\}$

The use of $[NEt_4]_2[ReBr_3(CO)_3]$, as the starting material leads to easy formation of the fac-$Re(CO)_3(L)_3$ core. The $[NEt_4]_2[ReBr_3(CO)_3]$ was readily derived from the $[ReBr(CO)_5]$. The synthesis of the Re(I) complexes was accomplished by reacting $[NEt_4]_2[ReBr_3(CO)_3]$ with the appropriate pyridine-2-methylamine in the ratio of 1:2 in 10 mL of $H_2O$. The reaction was allowed to heat at 80° C. for 3 hours. After cooling the reaction products were purified using a small silica column using 95% methylene chloride 5% methanol. X-ray quality crystals were grown by slow diffusion of pentane into a solution of the compound in methylene chloride.

EXAMPLE 16

Synthesis of $[Re(CO)_3\{(2-C_5H_4NCH_2)_2\}N—CH_3]$

The synthesis of the Re(I) complexes was accomplished by reacting $[NEt4]_2[ReBr_3(CO)_3]$ with the appropriate pyridine-2-methylamine in the ratio of 1:2 in 10 mL of $H_2O$. The reaction mixture was heated at 80° C. for 3 hours. After cooling, the reaction products were purified using a small silica column using methylene chloride(95%)/methanol (5%) as eluent. ESMS m/z=484 (observed).

EXAMPLE 17

Synthesis of [{N,N-di(pyridyl-2-methyl)}N-butyl-phthalimide] and Tc-99m labeling thereof The dipyridinemethylamine (0.5 g, 2.51 mmol) and N-(4-bromobutyl)-phthalimide (0.85 g, 3.02 mmol) were mixed in a 100 mL pressure tube in 2 mL of DMF. Potassium carbonate (0.05 g) was added to the solution. The mixture was heated at 120 C. for 1 hr. The reaction mixture was vacuumed down to residue. The residue was purified through a pad of silica gel using methanol-methylene chloride to provide the product in 41% yield. $^1H$ NMR($CDCl_3$): 1.57 (m), 2.54 (m), 2.85 (s), 2.93 (s), 3.58 (m), 3.76 (s), 7.09 (m), 7.52 (d), 7.61 (m), 7.68 (m), 7.80 (m), 7.99 (d), 8.44 (d).

$[^{99m}Tc(CO)_3(H_2O)_3]^+$ was heated with [{N,N-di(pyridyl-2-methyl)}]N-butyl-phthalimide in 0.5 mL (1 mg/mL) of methanol at 100° C. for 60 minutes. Purity, analyzed via C18 HPLC, showed >99% RCY. The product eluted with methanol at 20.8 minutes. The HPLC analysis was performed using a Supelco C18 column, 25 cm×4.6 mm column (5 μm pore size), equipped with 2 cm guard using solvent A=0.05 M triethylammonium phosphate buffer pH 2.5 and solvent B=methanol. The method employed was a gradient 5-95% B, 1 mL/minute for 30 minutes. The gradient ramped from 5-95 from 3-20 minutes. In challenge experiments the HPLC purified product demonstrated no degradation in either 10 mM Cysteine or Histidine in PBS pH 7.2 at 37° C. for 20 hrs.

EXAMPLE 18

Synthesis of Re and Tc Tricarbonyl Complexes of [ε-{N,N-di(pyridyl-2-methyl)α-(fmoc)lysine] (Fmoc-DpK)

[ε-{(N,N-di(pyridyl-2-methyl)}α-(fmoc)lysine] (Fmoc-DpK)

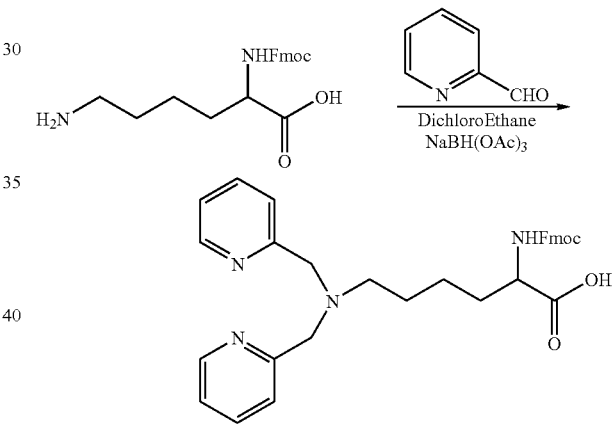

The fmoc-lysine, 2-pyridinecarboxaldehyde and sodium triacetoxyborohydride were mixed in 1,2-dichloroethane. The suspension was stirred at ambient temperature under an argon atmosphere for 1 hr. The reaction mixture was portioned between chloroform and water. The residue was purified through a pad of silica gel using methanol-chloroform to provide the product in 85% yield. Fmoc-deprotection employed stirring 4-dimethylaminopyridine in DMF/methanol at 25° C. for 12 hrs. Structural confirmation was performed by $^1H$ and $^{13}C$ NMR. $^1H$ NMR (δ(ppm), $CDCl_3$): 10.85 (bs, 1H, $CO_2H$), 8.50 (d, J=5.10 Hz, 2H, PyH), 7.70 (d, J=7.24 Hz, 2H, FlH), 7.55 (m, 4H, PyH, FlH), 7.46 (d, J=7.24, 2H, FlH), 7.32 (t, J=7.72, 2H, Py), 7.22(t, J=7.52, 2H, Py), 7.09 (t, J=6.20, 2H, FlH), 6.0 (d, J=9.31, 1H, NH), 4.29 (m, 3H, $OCH_2$, $NCHCO_2$), 4.17 (t, J=6.20,1H, CH), 3.86 (s, 4H, $PyCH_2$), 2.57 (t, 2H, $NCH_2$), 1.90-1.20 (m, 6H, $CH_2$). $^{13}C$ NMR ((δ(ppm), $CDCl_3$): 175.96 (C, $CO_2H$), 157.74 (2C, Py), 156.15 (C, CONH), 148.29 (2CH, Py), 144.12 (2C, Fl), 141.27(2C, Fl), 137.38 (2CH, Py), 127.68 (2CH, Py), 127.08 (2CH, Py), 125.26(2CH, Fl), 123.92 (2CH, Fl), 122.64(2CH, Fl), 119.96(2CH, Fl), 66.81(1C, OCH$_2$), 59.03 (2C, PyCH$_2$), 54.48 (C, NCHCO$_2$), 53.87 (C, NCH$_2$), 47.24 (C, Fl), 32.54 (C, CH$_2$), 26.04(C, CH$_2$), 22.86(C, CH$_2$).

[Re(CO)$_3${η$^3$-ε-[(N,N-di(pyridyl-2-methyl)]α(fmoc) lysine}][Br]

To a stirred solution of [NEt$_4$]$_2$[Re(CO)$_3$Br$_3$] (1.12 g, 1.45 mmol) in methanol (20 mL) was added [ε{N,N-di(pyridyl-2-methyl)}α-(fmoc)lysine](0.8 g, 1.45 mmol) in 2 mL methanol, whereupon the solution was refluxed for 5 hr and concentrated. The residue was dissolved in chloroform, washed with water, dried (NaSO$_4$) and evaporated to dryness to give a colorless product (1.04 g, 80%). $^1$H NMR (δ(ppm), MeOH-d$_4$): 8.88(d, J=5.29, 2H), 8.02-7.37 (m, 14H),5.05 (d, J=17.64 Hz, 2H, PyCH$_2$), 4.82 (d, J=17.64 Hz, 2H, PyCH$_2$), 4.44-4.35 (m, 4H), 3.88 (m, 2H), 2.20-1.50 (m, 6H, CH$_2$). $^{13}$C NMR (δ(ppm), MeOH-d$_4$): 197.47, 196.44 (fac-Re-CO$_3$), 175.42 (C, CO$_2$H), 161.82 (2C, Py), 158.30 (C, CONH),152.87 (2CH, Py), 145.13 (2C, FlH),142.29 (2C, FlH), 141.48 (2CH, Py), 129.07 (2CH, Py), 128.46 (2CH, Py), 126.94 (2CH, FlH), 126.58(2CH, FlH), 124.83 (2CH, FlH), 121.23(2CH, FlH), 71.66 (NCH$_2$), 68.72 (2C, PyCH$_2$), 67.70 (C, OCH$_2$), 55.27(NCHCO$_2$), 32.15(C, CH$_2$), 25.71 (2C,CH$_2$), 24.39(C, CH$_2$).

Tc-99m Labeling

[$^{99m}$Tc(CO)$_3$(H$_2$O)$_3$]$^+$ was heated with [ε-{N,N-di(pyridyl-2-methyl)}α-(fmoc)lysine] (DpK) in 0.5 mL (1 mg/mL) of methanol at 100° C. for 30 minutes. Purity, analyzed via C18 HPLC, showed >99% RCY. In challenge experiments the HPLC purified product demonstrated no degradation in either 100 mM Cysteine or Histidine in PBS pH 7.2 at 37° C. for 18 hrs. Labeling yields of >50% RCY, were achievable at levels as low as 2 µg /mL.

TABLE

Labeling results of Tc99m-DpK Complexes.

| Ligand Amounts (µg) | % Labeled Fmoc-DpK | % Labeled DpK |
|---|---|---|
| 500 | 100 | 100 |
| 100 | 100 | 47 |
| 10 | 93.9 | 32 |
| 1 | 52 | 16 |
| 0.1 | 7 | 5 |

EXAMPLE 19

Synthesis of Copper Complexes of Fmoc-DpK

[CuCl{η$^3$-ε-[(N,N-di(pyridyl-2-methyl)]α(fmoc) lysine}]

To a solution of CuCl$_2$ in 10 mL of methanol was added an excess of Fmoc protected dipyridine lysine (Fmoc-DpK). The solution was heated at 150 C for 3 hours in a 100 ml sealed pressure tube. Upon completion the solution was cooled and vaccuumed down to residue. The residue was dissolved in methylene chloride and layered with ether. After 12 hours a dark green-blue oil formed. The oil was sent out for ES/MS resulting in an observed masses of 648-650, which corresponds to the [CuCl(DpK)] complex. The oily product was cleaned up using a Waters C18 sep pak using 10% ethanol/ H$_2$O for the load. The purified product weighed 60 mg for 81% yield. $^1$H NMR (CDCl$_3$, 300 mhz, ppm) was performed: 1.23(m), 3.71(d), 3.83 (m), 4.19 (m), 4.35 (s), 7.13 (m), 7.26 (m), 7.35 (m), 7.46 (m), 7.51 (m), 7.61 (m), 7.72(m), 8.51(s). HPLC analysis was performed on a Vydac C18 column, 25 cm×4.6 mm column (5 µm pore size), equipped with 2 cm guard using solvent A=H2O+ 0.1% TFA B=CH3CN+0.1% TFA. The method employed was a gradient 15-80% B, 1 mL/ minute for 30 minutes. The gradient ramped from 15-80 from 3-22 minutes. The product eluted as two peaks (racemic mix of DpK ligand) at 19.3 and 19.6 minutes.

[$^{64}$CuCl{η$^3$-ε-[(N,N-di(pyridyl-2-methyl)]α(fmoc) lysine}]

$^{64}$CuCl$_2$ was heated with Fmoc protected dipyridine lysine (Fmoc-DpK) in 0.5 mL (100 µg/mL) of methanol at 70° C. for 20 minutes. Purity, analyzed via C18 HPLC, showed >85% RCY. The product eluted at 19.8 minutes.

EXAMPLE 20

Animal Studies

Biodistribution Summary for Tc-DPMAs

| Tc-Complex* | 5' HT/ BL Ratio | 60' HT/ BL Ratio | 5'% ID/g HT | 60'% ID/g HT |
|---|---|---|---|---|
| Tc-DPMA-I | 1.82 ± 0.44 | 4.70 ± 0.18 | 0.46 ± 0.08 | 0.37 ± 0.01 |
| Tc-DPMA-III | 0.50 ± 0.03 | 0.88 ± 0.04 | 0.21 ± 0.03 | 0.11 ± 0.01 |
| Tc-DPMA-V | 0.34 ± 0.03 | 6.49 ± 2.86 | 0.34 ± 0.01 | 0.24 ± 0.01 |

Tc-Complexes*:
Tc-DPMA-I = [($^{99m}$Tc(CO)$_3${(C$_5$H$_4$NCH$_2$)$_2$N)}],
Tc-DPMA-III = [($^{99m}$Tc(CO)$_3${(C$_5$H$_4$NCH$_2$)$_2$N((CH$_2$)$_2$COOCH$_2$CH$_3$)}],
Tc-DPMA-V = [($^{99m}$Tc(CO)$_3${(C$_5$H$_4$NCH$_2$)$_2$NCH$_2$CH$_2$CH$_2$N(CH$_3$)$_3$)}]

Biodistribution of Tc-99m-DpK

The biodistribution of Tc-99m-DpK was investigated in male rats (Sprague Dawley, n=5/timepoint, ~180 gms). The compound was injected via the tail vein in saline (10 µCi/100 µl). Animals were sacrificed at 5, 30, 60 and 120 minutes p.i. The results are shown in the Table.

TABLE

Selected Biodistribution results of Tc99m-DpK Complex, expressed as Average % ID/g ± (SEM).

| Organ | 5 Min ± (SEM) | 30 Min. ± (SEM) | 60 Min. ± (SEM) | 120 Min. ± (SEM) |
|---|---|---|---|---|
| Blood | 0.579 ± 0.051 | 0.069 ± 0.009 | 0.025 ± 0.005 | 0.013 ± 0.001 |
| Heart | 0.243 ± 0.020 | 0.034 ± 0.004 | 0.014 ± 0.001 | 0.008 ± 0.001 |
| Lung | 0.504 ± 0.023 | 0.076 ± 0.013 | 0.033 ± 0.002 | 0.021 ± 0.003 |
| Liver | 3.359 ± 0.442 | 2.748 ± 0.113 | 2.590 ± 0.077 | 2.119 ± 0.062 |
| Kidney | 6.053 ± 1.027 | 4.948 ± 0.106 | 4.931 ± 0.430 | 3.888 ± 0.419 |
| GI | 0.491 ± 0.081 | 0.886 ± 0.065 | 1.462 ± 0.085 | 2.725 ± 0.565 |

EXAMPLE 21

Both Tc-99m(DPMA) (1) and Tc-99m(DPMA ethyl ester) (6) were investigated as potential heart imaging agents on their own in a group of rats. The vertebrate animals in this research project were used to investigate the biodistribution and pharmacokinetics of new technetium-DPMA complexes and determine uptake in the heart. Rats (Sprague Dawley, male, at 80-100 grams each) were used for the whole body biodistribution studies. The compounds were evaluated at two time points, i.e., 5 and 60 minutes, with four animals per time point. The use of this number of animals provided accurate statistics in the clearance rate measurements, and accounted for intraspecies variation. The preliminary results are tabulated below.

Selected Biodistribution Results from Rat Studies Examining Myocardium Uptake

| Tc-Complex | HT/BL Ratio at 5 min. | HT/BL Ratio at 60 min. | % DPG Heart at 5 min. | % DPG Heart at 60 min. |
|---|---|---|---|---|
| Tc-DPMA (1) | 1.82 | 4.700 | 0.462 | 0.367 |
| Tc-DPMA ethyl ester (6) | 0.499 | 0.881 | 0.208 | 0.111 |

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A complex comprising a radionuclide complexed with a compound represented by A:

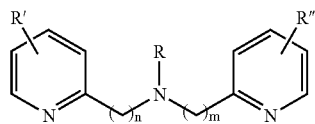

wherein:
R is selected from the group consisting of H, alkyl, hydroxyalkyl, alkoxyalkyl, aminoalkyl, thioalkyl, alkenyl, alkynyl, aryl, heteroaryl, aralkyl, heteroaralkyl, acyl, aminoacyl, hydroxyacyl, thioacyl, —CO$_2$H, —(CH$_2$)$_d$—R$_{80}$, and an amino acid radical;
R' is absent or present from 1 to 4 times;
R" is absent or present from 1 to 4 times;
each instance of R' or R" is selected independently from the group consisting of halogen, alkyl, alkenyl, alkynyl, hydroxyl, alkoxyl, acyl, acyloxy, acylamino, silyloxy, amino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, cyano, guanidine, amidine, acetal, ketal, amine oxide, aryl, heteroaryl, aralkyl, heteroaralkyl, azido, aziridine, carbamoyl, epoxide, hydroxamic acid, imide, oxime, sulfonamide, thioamide, thiocarbamate, urea, thiourea, and —(CH$_2$)$_d$—R$_{80}$;
R$_{80}$ represents independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, peptide, saccharide, ribonucleic acid, or (deoxy)ribonucleic acid;
d is an integer in the range 0 to 12 inclusive;
m is an integer in the range 0 to 6 inclusive; and
n is an integer in the range 0 to 6 inclusive.

2. The complex of claim 1, wherein said radionuclide is technetium or rhenium.
3. The complex of claim 1, wherein m is 1.
4. The complex of claim 1, wherein n is 1.
5. The complex of claim 1, wherein m is 1; and n is 1.
6. The complex of claim 1, wherein R' is absent.
7. The complex of claim 1, wherein R" is absent.
8. The complex of claim 1, wherein R' is absent; and R" is absent.
9. The complex of claim 1, wherein m is 1; n is 1; R' is absent; and R" is absent.
10. The complex of claim 1, wherein R is —(CH$_2$)$_d$—R$_{80}$.
11. The complex of claim 1, wherein m is 1; n is 1; R' is absent; R" is absent; and R is —(CH$_2$)$_d$—R$_{80}$.
12. The complex of claim 1, wherein m is 1; n is 1; R' is absent; R" is absent; and R is —(CH$_2$)$_d$—R$_{80}$; wherein said radionuclide is technetium or rhenium.
13. The complex of claim 1, wherein R is an amino acid radical.
14. The complex of claim 1, wherein R is an amino acid radical; m is 1; and n is 1.
15. The complex of claim 1, wherein R is an amino acid radical; m is 1; n is 1; R' is absent; and R" is absent.
16. The complex of claim 1, wherein R is an amino acid radical; m is 1; n is 1; R' is absent; and R" is absent; wherein said radionuclide is technetium or rhenium.
17. The complex of claim 1, wherein the amino acid radical is —CH$_2$CH$_2$CH$_2$CH$_2$CH(NH$_2$)CO$_2$H.
18. The complex of claim 1, wherein the amino acid radical is —CH(CO$_2$H)CH$_2$CH$_2$CH$_2$CH$_2$NH$_2$.
19. The complex of claim 1, wherein the amino acid radical is —CH$_2$CH$_2$CO$_2$H.
20. The complex of claim 1, wherein the amino acid radical is —CH(CO$_2$H)(CH$_2$)$_x$CH(NH$_2$)CO$_2$H, wherein x is an integer from 3 to 9 inclusively.
21. A formulation, comprising a complex according to any of claims 1, 2-11, 12-15, or 16-20; and a pharmaceutically acceptable excipient.
22. A method of imaging a region in a patient, comprising the steps of: administering to a patient a diagnostically effective amount of a complex of claim 1; and obtaining an image of said region of said patient.
23. The method of claim 22, wherein said region of said patient is the head or thorax.
24. A method of preparing a peptide conjugate incorporating a complex of claim 13 wherein the peptide conjugate is prepared using solid phase synthetic techniques.

* * * * *

UNITED STATES PATENT AND TRADEMARK OFFICE
CERTIFICATE OF CORRECTION

PATENT NO. : 7,381,399 B2  Page 1 of 1
APPLICATION NO. : 10/386403
DATED : June 3, 2008
INVENTOR(S) : John W. Babich et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 634 days.

should read (*) Notice: Subject to any disclaimer, the term of this patent is extended or adjusted under 35 U.S.C. 154(b) by 1,303 days.

Signed and Sealed this

Eleventh Day of May, 2010

David J. Kappos
*Director of the United States Patent and Trademark Office*